United States Patent
Blumberg et al.

(10) Patent No.: US 10,822,417 B2
(45) Date of Patent: Nov. 3, 2020

(54) HUMANIZED AFFINITY MATURED ANTI-FCRN ANTIBODIES

(71) Applicant: Syntimmune, Inc., Boston, MA (US)

(72) Inventors: Laurence J. Blumberg, New York, NY (US); Richard S. Blumberg, Weston, MA (US); Susan D. Jones, Boston, MA (US); Derry Roopenian, Salsbury Cove, ME (US); Robert George E. Holgate, Royston (GB); Timothy D. Jones, Cambridge (GB); Arron R. Hearn, Ely (GB)

(73) Assignee: Syntimmune, Inc., Boston, MA (US)

( * ) Notice: Subject to any disclaimer, the term of this patent is extended or adjusted under 35 U.S.C. 154(b) by 131 days.

(21) Appl. No.: 16/096,311

(22) PCT Filed: Apr. 25, 2017

(86) PCT No.: PCT/US2017/029375
§ 371 (c)(1),
(2) Date: Oct. 25, 2018

(87) PCT Pub. No.: WO2017/189556
PCT Pub. Date: Nov. 2, 2017

(65) Prior Publication Data
US 2019/0135915 A1 May 9, 2019

Related U.S. Application Data

(60) Provisional application No. 62/326,907, filed on Apr. 25, 2016.

(51) Int. Cl.
| C07K 16/28 | (2006.01) |
| G01N 33/68 | (2006.01) |
| A61P 39/00 | (2006.01) |
| A61K 31/19 | (2006.01) |
| A61K 38/38 | (2006.01) |
| A61K 39/395 | (2006.01) |
| A61K 39/00 | (2006.01) |

(52) U.S. Cl.
CPC ............ *C07K 16/283* (2013.01); *A61K 31/19* (2013.01); *A61K 38/38* (2013.01); *A61K 39/3955* (2013.01); *A61P 39/00* (2018.01); *C07K 16/28* (2013.01); *G01N 33/6854* (2013.01); *G01N 33/6872* (2013.01); *A61K 2039/505* (2013.01); *C07K 2317/24* (2013.01); *C07K 2317/51* (2013.01); *C07K 2317/565* (2013.01); *C07K 2317/92* (2013.01); *C07K 2317/94* (2013.01); *G01N 2333/70535* (2013.01); *G01N 2333/765* (2013.01)

(58) Field of Classification Search
CPC ........ A61K 2039/505; A61K 2039/507; A61K 2039/545; A61K 35/17; A61K 39/39558; A61K 45/06; A61K 31/19; A61K 38/38; C07K 2317/24; C07K 2317/565; C07K 2317/92; C07K 16/2803; C07K 16/2818; C07K 16/2827; C07K 16/3007; C07K 2317/58; C07K 2317/567; C07K 2317/73; C07K 2317/90; C07K 16/28; C07K 16/283; C07K 2317/51; C07K 2317/94
See application file for complete search history.

(56) References Cited

U.S. PATENT DOCUMENTS

| 2010/0209424 A1 | 8/2010 | Roopenian et al. |
| 2010/0216187 A1 | 8/2010 | Lasters et al. |
| 2012/0107845 A1 | 5/2012 | Blumberg et al. |
| 2014/0308206 A1 | 10/2014 | Sexton et al. |
| 2015/0118240 A1 | 4/2015 | Finney et al. |

FOREIGN PATENT DOCUMENTS

| WO | 2015/071330 A1 | 5/2015 |
| WO | 2015/164364 A2 | 10/2015 |
| WO | 2015/167293 A1 | 11/2015 |
| WO | 2016/1833352 A1 | 11/2016 |

OTHER PUBLICATIONS

Anderson, C. L et al., "Perspective—FcRn Transports Albumin: Relevance to Immunology and Medicine"; Trends in Immunology (2006); vol. 27:7; pp. 343-348.

Christianson, G. J. et al., "Monoclonal Antibodies Directed Against Human FcRn and Their Applications"; Landes Bioscience (2012); vol. 4:2; pp. 208-216.

Sands, K. et al. "Dissection of the Neonatal Fc Receptor (FcRn)-Albumin Interface Using Mutagenesis and Anti-FcRn Albumin-Blocking Antibodies"; The Journal of Biological Chemistry (2014); vol. 289:24; pp. 17228-17239.

*Primary Examiner* — Padmavathi Baskar
(74) *Attorney, Agent, or Firm* — Fox Rothschild LLP

(57) ABSTRACT

Provided herein are recombinant antibodies and antigen-binding portions thereof useful for binding to FcRn and blocking binding of FcRn to human serum albumin. The FcRn-binding proteins can be used to treat a variety of disorders including acute and chronic toxic exposure.

9 Claims, 10 Drawing Sheets

Specification includes a Sequence Listing.

| Kabat No. | | 1 2 3 4 5 6 7 8 9 | 1<br>0 1 2 3 4 5 6 7 8 9 | 2<br>0 1 2 3 4 5 6 7 8 9 | 3<br>0 1 2 3 4 5 6 7 8 9 0 | 1 2 3 4 5 A B | 4<br>6 7 8 9 0 1 2 3 |
|---|---|---|---|---|---|---|---|
| SEQ ID NO. | ADM31 | E V Q L V E S G G | G L V K P G G S L K L S C A A S G F T F S | X X X X X X | W V R Q A P E K |
| | VH1 | E V Q L V E S G G | G L V K P G G S L K L S C A A S G F T F S | X X X X X X – – | W V R Q A P G K |
| | VH3 | E V Q L V E S G G | G L V K P G G S L K L S C A A S G F T F S | X X X X X – – – | W V R Q A P G K |
| | VH4 | E V Q L V E S G G | G L V K P G G S L K L S C A A S G F T F S | X X X X X – – – | W V R Q A P G K |

| Kabat No. | | 5<br>4 5 6 7 8 9 | 5<br>0 1 2 A B C 3 4 5 | 6<br>6 7 8 9 0 1 2 3 4 5 | 6<br>6 7 8 9 0 1 2 3 4 5 | 7<br>6 7 8 9 0 1 2 3 | 8<br>4 5 6 7 8 9 0 1 2 A B C |
|---|---|---|---|---|---|---|---|
| SEQ ID NO. | ADM31 | G L E W V A | X X X | X X X X X X X X X X X X | X X X | R F T I S R D N A K N T L F L Q M T S L |
| | VH1 | G L E W V A | X X X | X X X X X X X X X X X X | X X | R F T I S R D N A K N T L Y L Q M N S L |
| | VH3 | G L E W V A | X X X | X X X X X X X X X X X X | X X | R F T I S R D N A K N T L Y L Q M N S L |
| | VH4 | G L E W V A | X X X | X X X X X X X X X X X X | X X | R F T I S R D N A K N T L Y L Q M N S L |

| Kabat No. | | 9<br>3 4 5 6 7 8 9 0 1 2 3 4 | 10<br>5 6 7 8 9 0 A B C D E F G H I J K 1 2 | 3 4 5 | 11<br>6 7 8 9 0 1 2 3 |
|---|---|---|---|---|---|
| SEQ ID NO. | ADM31 | R S E D T A M Y Y C A R | X X X X X X X X X X X X X X X X X X X | X X | W G Q G T S V T V S S |
| | VH1 | R A E D T A M Y Y C A R | X X X X X X X X X X X X X X X X X X X | X X | W G Q G T S V T V S S |
| | VH3 | R A E D T A V Y Y C A R | X X X X X X X X X X X X X X X X X X X | X X | W G Q G T T V T V S S |
| | VH4 | R S E D T A M Y Y C A R | X X X X X X X X X X X X X X X X X X X | X X | W G Q G T T V T V S S |

```
Kabat                    1
No.       1 2 3 4 5 6 7 8 9 0 1 2 3 4 5 6 7 8 9 0 1 2 3
SEQ ID NO:
ADM31     S I V M T Q T P K F L L V S A G D R V T I T C
VK1       S I V M T Q S P D F L L A S V G D R V T I T C
VK2       S I V M T Q S P D S L S A S V G D R V T I T C
VK3       D I V M T Q S P D S L S A S V G D R V T I T C
VK4       D I V M T Q S P D S L S A S V G D R V T I T C Kabat                        2                       3
No.       4 5 6 7 A B C D E F 8 9 0 1 2 3 4 5 6 7
SEQ ID NO:
ADM31     K A S Q             S V S N D V A W Y Q
VK1       K A S Q             S V S N D V A W Y Q
VK2       K A S Q             S V S N D V A W Y Q
VK3       K A S Q             S V S N D V A W Y Q
VK4       K A S Q             S V S N D V A W Y Q Kabat           4                           5
No.       8 9 0 1 2 3 4 5 6 7 8 9 0 1 2 3 4 5 6 7 8 9
SEQ ID NO:
ADM31     Q K P G Q S P K L L I Y Y A S N R Y T
VK1       Q K P G Q P P K L L I Y Y A S N R Y T
VK2       Q K P G Q P P K L L I Y Y A S N R Y T
VK3       Q K P G Q P P K L L I Y Y A S N R Y T
VK4       Q K P G Q P P K L L I Y Y A S N R Y T Kabat       6                       7
No.       0 1 2 3 4 5 6 7 8 9 0 1 2 3 4 5 6 7 8
SEQ ID NO:
ADM31     G V P D R F T G S G Y G T D F T F T I S T V Q A
VK1       G V P D R F T G S G Y G T D F T L T I H S S L Q A
VK2       G V P D R F T G S G Y G T D F T L T I H S S L Q A
VK3       G V P D R F S G S G Y G T D F T L T I S S L Q A
VK4       G V P D R F S G S G Y G T D F T L T I S S L Q A Kabat             9                 1
No.       0 1 2 3 4 5 6 7 8 9 0 1 2 3 4 5 6 7 8
SEQ ID NO:
ADM31     E D L A V Y F C Q Q D Y S S L T F G A G T K L E L K
VK1       E D V A V Y F C Q Q D Y S S L T F G Q G T K L E I K
VK2       E D V A V Y F C Q Q D Y S S L T F G Q G T K L E I K
VK3       E D V A V Y F C Q Q D Y S S L T F G Q G T K L E I K
VK4       E D V A V Y Y C Q Q D Y S S L T F G Q G T K L E I K
```

HUMANIZED AFFINITY MATURED ANTI-FCRN ANTIBODIES

This application claims priority to U.S. Application No. 62/326,907, filed Apr. 25, 2016, which is incorporated herein in its entirety.

FIELD OF THE INVENTION

The invention relates to antibodies and antigen-binding portions thereof that bind to FcRn and their use for modulating or inhibiting interaction of FcRn with albumin. The antibodies are useful as therapeutics for minimizing the toxic effects of certain compounds or molecules that bind albumin.

SEQUENCE LISTING

The instant application contains a Sequence Listing which has been submitted in ASCII format via EFS-Web and is hereby incorporated by reference in its entirety. The Sequence Listing, created on Apr. 25, 2017, is named 162255.46276_Sequence-Listing.txt and is 58,787 bytes in size.

BACKGROUND OF THE INVENTION

The neonatal Fc receptor (FcRn) is an intracellular trafficking integral membrane Fc receptor for IgG. FcRn was originally identified as a receptor functioning in neonatal life. It was first isolated from rodent gut as a heterodimer between a 12 kDa and a 40-50 kDa protein (Rodewald & Kraehenbuhl 1984, J. Cell. Biol. 99(1 Pt2): 159s-154s; Simister & Rees, 1985, Eur. J. Immunol. 15:733-738) and was cloned in 1989 (Simister & Mostov, 1989, Nature 337:184-187). Cloning and subsequent crystallization of FcRn revealed it to have an approximately 50 kDa major histocompatibility complex (MHC) class I-like heavy chain in non-covalent association with a 12 kDa β2-microglobulin light chain (Raghavan et al., 1993, Biochemistry 32:8654-8660; Huber et al., 1993, J. Mol. Biol. 230:1077-1083). Although first recognized in connection with fetal and neonatal life, FcRn is today known to continue to function throughout adult life. FcRn resides primarily in the early acidic endosomes where it binds to the Fc region of IgG in a pH-dependent manner, with micro- to nanomolar affinity at pH 6.5, while binding of FcRn to Fc at physiological pH is negligible. The bulk of FcRn is present in endosomes in most cells, and the interaction between FcRn and its IgG Fc ligands occurs within that acidic environment. In some cells, such as hematopoietic cells, significant levels of FcRn can be detected on the cell surface in addition to intracellular expression (Zhu et al., 2001, J. Immunol. 166:3266-3276). In this case, when the extracellular milieu is acidic, as in the case of neoplastic or infectious conditions, it is possible that FcRn can bind to IgG on the cell surface of these cell types. FcRn regulates serum IgG concentrations by binding to and protecting endocytosed monomeric IgG from degradation in the lysosomal compartment, and transporting the IgG to the cell surface for release at neutral extracellular pH. Through this mechanism, FcRn is responsible for the long serum half-life of IgG, since IgG that is not bound by FcRn enters the lysosomal pathway and is degraded.

FcRn contains a binding site for albumin that is distinct from its binding site for the Fc domain of IgG, due to ionic interactions between FcRn and IgG or albumin on opposite faces of the FcRn heavy chain (Chaudhury et al., 2006, Biochemistry 45:4983-4990). Like its binding to IgG, binding of FcRn to albumin is strongly pH-dependent, occurring at acidic pH (typically less than pH 6, and optimally at pH 5) but not at neutral pH. FcRn binding of albumin protects albumin from degradation and results in an extended serum half-life for albumin. In the absence of FcRn expression in mice, albumin is lost into the bile from circulation. (Kim et al., 2006, Am J Gastrointest Liver Phsiol 290(2):G352-60). Further, there is increasing evidence that albumin is pathogenic in multiple disease settings, for example acute and chronic toxic exposures (Taguchi, J Pharm Sci 2012), atherosclerotic coronary and peripheral vascular disease (Song, Atherosclerosis 2012), diabetic vasculopathic complications (Kim, Diab Metab J 2012; Murea, Am J Nephrol 2012), and Alzheimer's disease (Byun, PLoS One 2012).

SUMMARY OF THE INVENTION

The present invention provides antibodies and antigen-binding portions thereof that bind to FcRn. The antibodies bind to an epitope of FcRn that overlaps the binding site for the Fc domain of albumin and reduce or inhibit binding of FcRn to albumin.

Provided herein is an antibody or antigen-binding fragment thereof which binds to FcRn comprising a heavy chain variable region, the heavy chain variable region comprising CDR1, CDR2, and CDR3, wherein:
  the sequence of CDR1 is SEQ ID NO:2;
  the sequence of CDR2 is SEQ ID NO:4; and
  the sequence of CDR3 is SEQ ID NO:48.

In one embodiment, the sequence of CDR3 is SEQ ID NO:46. In another embodiment, the sequence of CDR3 is SEQ ID NO:44.

In other embodiments, the sequence of CDR3 is selected from the group consisting of SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:44, SEQ ID NO:46, and SEQ ID NO:48. In one embodiment, the sequence of CDR3 is SEQ ID NO:27 or SEQ ID NO:31.

Also provided herein is an antibody or antigen-binding fragment thereof which binds to FcRn comprising a heavy chain variable region and a light chain variable region, wherein each of the heavy chain and the light chain variable regions comprises CDR1, CDR2, and CDR3, and wherein:
  the sequence of CDR1 of the heavy chain is SEQ ID NO:2;
  the sequence of CDR2 of the heavy chain is SEQ ID NO:4; and
  the sequence of CDR3 of the heavy chain is selected from the group consisting of SEQ ID NO:25, SEQ ID NO:27, SEQ ID NO:29, SEQ ID NO:31, SEQ ID NO:33, SEQ ID NO:35, SEQ ID NO:37, SEQ ID NO:39; and
  the sequence of CDR1 of the light chain is SEQ ID NO:6;
  the sequence of CDR2 of the light chain is SEQ ID NO:8; and
  the sequence of CDR3 of the light chain is SEQ ID NO:10.

In some embodiments, the sequence of CDR3 of the heavy chain is SEQ ID NO:27 or SEQ ID NO:31.

In some embodiments, the antibody or antigen-binding fragment herein is a chimeric or humanized antibody or antigen-binding fragment.

Also provided herein is an antibody or antigen-binding fragment thereof which binds to FcRn comprising a heavy chain variable region, wherein the sequence of the heavy chain variable region is SEQ ID NO:26, SEQ ID NO:28, SEQ ID NO:30, SEQ ID NO:32, SEQ ID NO:34, SEQ ID NO:36, SEQ ID NO:38, or SEQ ID NO:40, or the sequence of the heavy chain variable region is at least 95% identical to the heavy chain variable region amino acid sequence of SEQ ID NO:26, SEQ ID NO:28, SEQ ID NO:30, SEQ ID NO:32, SEQ ID NO:34, SEQ ID NO:36, SEQ ID NO:38, or SEQ ID NO:40.

In some embodiments, the antibody or antigen-binding fragment further comprises a light chain variable region, wherein the sequence of the light chain variable region is SEQ ID NO:22. In some embodiments, the sequence of the heavy chain variable region is SEQ ID NO:28 or SEQ ID NO:32. In some embodiments, the sequence of the heavy chain variable region is SEQ ID NO:28. In other embodiments, the sequence of the heavy chain variable region is SEQ ID NO:32.

Also provided is an antibody or antigen-binding fragment thereof which binds to FcRn comprising a light chain variable region, wherein the sequence of the light chain variable region is SEQ ID NO:18, SEQ ID NO:20, SEQ ID NO:22, or SEQ ID NO:24, or the sequence of the light chain variable region is at least 95% identical to the light chain variable region amino acid sequence of SEQ ID NO:18, SEQ ID NO:20, SEQ ID NO:22, or SEQ ID NO:24. In some embodiments, the sequence of the light chain variable region is SEQ ID NO:22. In some embodiments, the sequence of the light chain variable region is SEQ ID NO:22 and the antibody or antigen-binding fragment further comprises a heavy chain variable region, wherein the heavy chain variable region comprises the framework region of SEQ ID NO:12. In some embodiments, the sequence of the light chain variable region is SEQ ID NO:22 and the antibody or antigen-binding fragment further comprises a heavy chain variable region, wherein the sequence of the heavy chain variable region is SEQ ID NO:28. In other embodiments, the sequence of the light chain variable region is SEQ ID NO:22 and the antibody or antigen-binding fragment further comprises a heavy chain variable region, wherein the sequence of the heavy chain variable region is SEQ ID NO:32.

Also provided herein is an antibody or antigen-binding fragment thereof which binds to FcRn comprising a heavy chain variable region, wherein the heavy chain variable region comprises the framework region of the heavy chain variable region amino acid sequence of SEQ ID NO:12, SEQ ID NO:14, or SEQ ID NO:16, or a framework region that is at least 95% identical to the framework region of SEQ ID NO:12, SEQ ID NO:14, or SEQ ID NO:16. In some embodiments, the heavy chain variable region comprises the framework region of the heavy chain variable region amino acid sequence of SEQ ID NO:12, or a framework region that is at least 95% identical to the framework region of SEQ ID NO:12.

Also provided is an antibody or antigen-binding fragment thereof which binds to FcRn comprising a light chain variable region, wherein the light chain variable region comprises the framework region of the light chain variable region amino acid sequence of SEQ ID NO:18, SEQ ID NO:20, SEQ ID NO:22, or SEQ ID NO:24, or a framework region that is at least 95% identical to the framework region of SEQ ID NO:18, SEQ ID NO:20, SEQ ID NO:22, or SEQ ID NO:24. In some embodiments, the light chain variable region comprises the framework region of the light chain variable region amino acid sequence of SEQ ID NO:22, or a framework region that is at least 95% identical to the framework region of SEQ ID NO:22.

In some embodiments of the antibodies described herein, the antibody has isotype IgG4. In some embodiments, the antibody contains S241P modifications in the heavy chains. In some embodiments, the antibody lacks C-terminal lysines in the heavy chains. In some embodiments, the antibody contains S241P modifications in the heavy chains and lacks C-terminal lysines in the heavy chains.

In some embodiments, the antibody or antigen-binding fragment described herein is an scFv, Fv, Fab', Fab, F(ab')$_2$, or diabody.

Also provided herein is an antibody that competes with or cross-blocks an antibody or antigen-binding fragment thereof which binds to FcRn described herein.

Also provided herein is an isolated nucleic acid encoding an FcRn antibody or antigen-binding fragment described herein. Also provided herein is a nucleic acid vector comprising an isolated nucleic acid encoding an FcRn antibody or antigen-binding fragment described herein. Also provided herein is a prokaryotic or eukaryotic host cell comprising an isolated nucleic acid encoding an FcRn antibody or antigen-binding fragment described herein. Also provided herein is a composition comprising an FcRn antibody or antigen-binding fragment described herein and a pharmaceutically acceptable carrier.

Also provided herein is a method of modulating the interaction between FcRn and albumin which comprises contacting FcRn with an antibody or antigen-binding fragment described herein.

Also provided herein is a method of reducing levels of albumin in a subject which comprises administering to the subject an amount of an antibody or antigen-binding fragment described herein effective to reduce levels of albumin. In some embodiments, the subject is a mammal. In some embodiments, the mammal is a human.

Also provided herein is a method of reducing levels of albumin-bound toxins in a subject which comprises administering to the subject an amount of an antibody or antigen-binding fragment described herein effective to reduce levels of albumin-bound toxins. In some embodiments, the albumin-bound toxin may be exogenous or endogenous. In some embodiments, the albumin-bound toxin is copper, hematin, long-chain fatty acid, zinc, bilirubin, thyroxine, eicosanoids, tryptophan, vitamin D3, bile acids, calcium, magnesium, chloride, indomethacin, bromphenol blue, salicylate, warfarin, phenylbutazone, digoxin, furosemide, phenytoin, chlorpropamide, benzylpenicillin, Evans blue, diazepam, ibuprofen, naproxen, clofibrate, chlorpromazine, imipramine, quinidine, ricin, amiodarone, or acetaminophen. In some embodiments, the albumin-bound toxin may be acetaminophen. In some embodiments, a therapeutically effective amount of an antibody or antigen-binding portions thereof set forth herein may be administered in combination (e.g. simultaneously, sequentially, or separately) with other agents, drugs, or hormones. In some embodiments, the known therapies may be the standard of care. For example, in embodiments wherein the albumin-bound toxin may be acetaminophen, the method may further comprise the simultaneous, separate, or sequential administration of N-acetyl cysteine.

Also provided herein are methods of preventing, treating, inhibiting, or reducing exposure to a toxin in a subject which comprise administering to the subject an effective amount of an antibody or antigen-binding fragment described herein. In some embodiments, the albumin-bound toxin may be exogenous or endogenous. In some embodiments, the toxin is copper, hematin, long-chain fatty acid, zinc, bilirubin, thyroxine, eicosanoids, tryptophan, vitamin D3, bile acids, calcium, magnesium, chloride, indomethacin, bromphenol blue, salicylate, warfarin, phenylbutazone, digoxin, furosemide, phenytoin, chlorpropamide, benzylpenicillin, Evans blue, diazepam, ibuprofen, naproxen, clofibrate, chlorpromazine, imipramine, quinidine, ricin, amiodarone, or acetaminophen. In some embodiments, the albumin-bound toxin may be acetaminophen. In some embodiments, a therapeutically effective amount of an antibody or antigen-binding portions thereof set forth herein may be administered in combination (e.g. simultaneously, sequentially, or separately) with other agents, drugs, or hormones. In some embodiments, the known therapies may be the standard of care. For example, in embodiments wherein the albumin-bound toxin may be acetaminophen, the method may further comprise the simultaneous, separate, or sequential administration of N-acetyl cysteine.

Also provided herein are methods of preventing or treating a medical condition associated with albumin toxicity which comprise administering to the subject an effective amount of an antibody or antigen-binding fragment described herein. In some embodiments, the medical condition is atherosclerotic coronary and peripheral vascular disease. In some embodiments, the medical condition is diabetic vasculopathic complications. In some embodiments, the medical condition is Alzheimer's disease. In some embodiments, the medical condition is traumatic brain injury. In some embodiments, the medical condition is diabetes mellitus. In some embodiments, the medical condition is end-stage kidney failure. In some embodiments, a therapeutically effective amount of an antibody or antigen-binding portions thereof set forth herein may be administered in combination (e.g. simultaneously, sequentially, or separately) with other agents, drugs, or hormones. In some embodiments, the other agents, drugs, or hormones may be known therapies for the respective medical condition. In some embodiments, the known therapies may be the standard of care.

Also provided herein is a method of promoting endogenous albumin degradation prior to the administration of an albumin-based therapeutic comprising administering an anti-FcRn antibody or fragment thereof that is specific for the albumin binding site of FcRn to a subject in need of treatment with the albumin-based therapeutic prior to administering the albumin-based therapeutic.

Also provided herein is a method of promoting degradation of an exogenous albumin-based therapeutic that has been administered to a subject, which comprises administering to the subject an effective amount of an anti-FcRn antibody or fragment thereof that is specific for the albumin binding site of FcRn.

In some embodiments, the method further comprises the step of administering the albumin-based therapeutic to the subject. In some embodiments, the pharmacokinetics or pharmacodynamics of the albumin-based therapeutic is enhanced.

BRIEF DESCRIPTION OF THE FIGURES

FIG. 1 shows the amino acid sequences of humanized heavy chain variants ($V_H1$, $V_H1$, and $V_H4$). The variants are based on human heavy chain variable domain sequences and are aligned to show changes in amino acids incorporated at certain positions to minimize potential immunogenicity. Amino acid residues that vary among the humanized frameworks are underlined. Kabat CDRs are boxed.

FIG. 2 shows the amino acid sequences of humanized light chain variants (Vκ1-Vκ4). The variants are based on human light chain variable domain sequences and are aligned to show changes in amino acids incorporated at certain positions to minimize potential immunogenicity Amino acid residues that vary among the humanized frameworks are underlined. Kabat CDRs are boxed.

DETAILED DESCRIPTION

Figure 3:
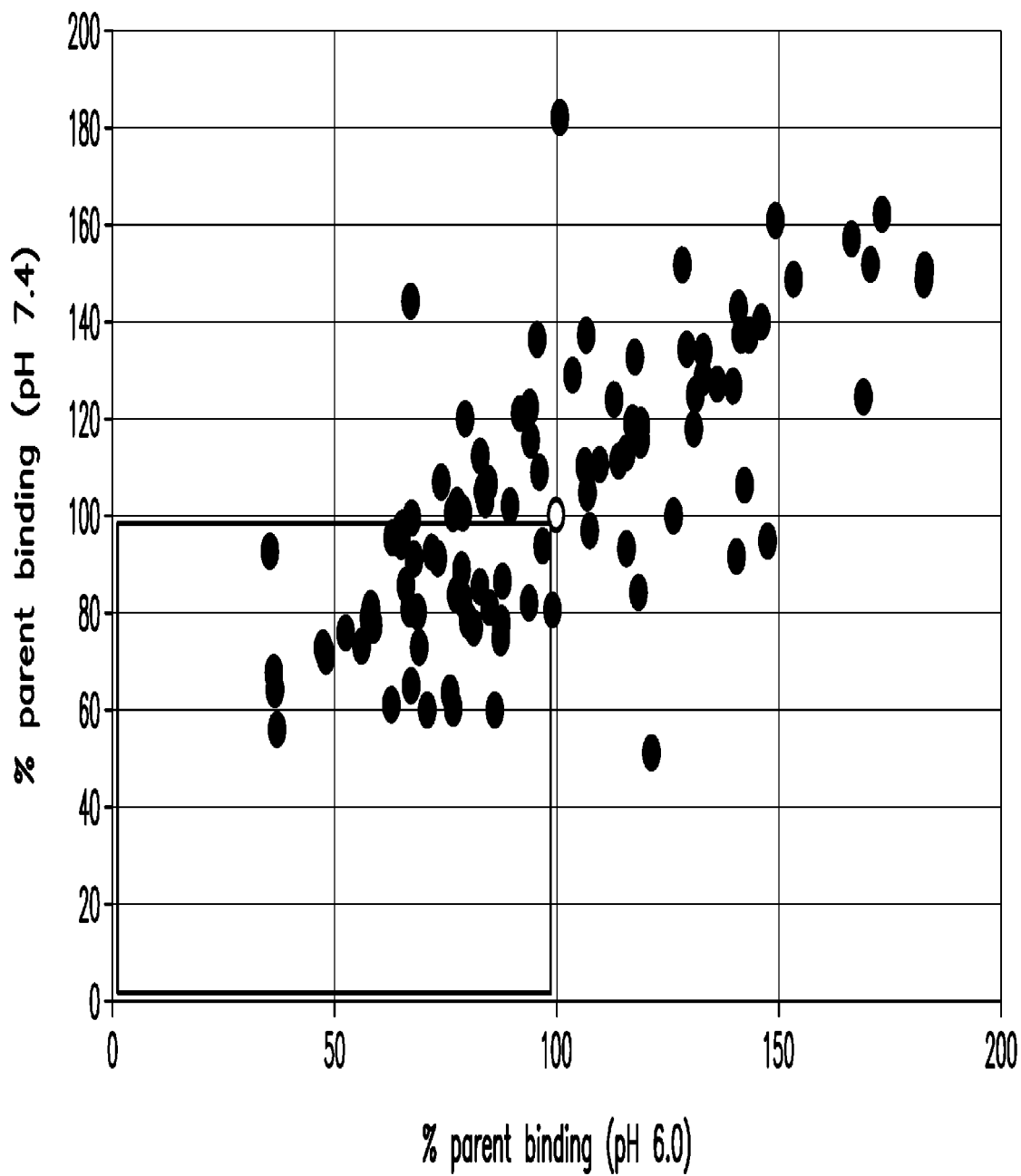
FIG. 3 shows a comparison of competition ELISAs at pH 6.0 and pH 7.4. The parent scFv is shown in the center. scFvs of interest for further analysis are highlighted by the box.

In one aspect, provided herein are antibodies and binding proteins that bind to FcRn. More particularly, the antibodies bind to an epitope of FcRn that overlaps the binding site for albumin Consequently, the antibodies modulate FcRn-mediated functions, such as binding of FcRn to albumin, protection of albumin from degradation, and half-life extension of albumin-bound compounds. In another aspect, provided is an isolated nucleic acid comprising a sequence that encodes an FcRn antibody or antigen-binding portion thereof. In another aspect, provided is a composition suitable for administration to a subject which comprises and FcRn antibody or antigen-binding portion thereof and a pharmaceutically acceptable carrier.

In some embodiments, the antibodies disclosed herein inhibit the binding of albumin to human FcRn but do not inhibit the binding of human IgG to human FcRn. In some embodiments, the antibodies disclosed herein decrease the serum half-life of albumin but do not decrease the serum half-life of human IgG.

In another aspect, provided are methods of modulating the interaction between FcRn and albumin. For example, by reducing binding of albumin to FcRn, the antibodies or antigen-binding portions thereof set forth herein can be used to reduce the half-life of circulating albumin and treat or prevent acute and chronic toxic exposures. Albumin is known to bind a wide range of compounds and molecules, for example, copper, hematin, long-chain fatty acid, zinc, bilirubin, thyroxine, eicosanoids, tryptophan, vitamin D3, bile acids, calcium, magnesium, chloride, indomethacin, bromphenol blue, salicylate, warfarin, phenylbutazone, digoxin, furosemide, phenytoin, chlorpropamide, benzylpenicillin, Evans blue, diazepam, ibuprofen, naproxen, clofibrate, chlorpromazine, imipramine, and quinidine (see, e.g., Varshney et al., Ligand binding strategies of human serum albumin: How can the cargo be optimized. Chirality. 2010(22):77-87). Ricin is also known to bind to albumin (Blome and Schengrund., Toxicon. 2008 51(7):1214-24). Also, acetaminophen has been found to bind human serum albumin (Damsten et al., Drug Metab Dispos. 2007 35(8): 1408-17). Excretion of such compounds and molecules would be advantageous in the treatment of various conditions including, without limitation, toxic overdoses of a variety of drugs (e.g., albumin conjugated medications and fusion proteins), heavy metal toxicity, bacterial overload, bacterial sepsis, and a variety of other conditions.

Similarly, the antibodies or antigen-binding portions thereof set forth herein may be used to reduce the half-life of circulating albumin for the treatment of medical conditions associated with albumin toxicity or for which lower levels have been indicated to be beneficial. For example, albumin has been implicated in atherosclerotic coronary and peripheral vascular disease (Song, Atherosclerosis 2012), diabetic vasculopathic complications (Kim, Diab Metab J 2012; Murea, Am J Nephrol 2012), Alzheimer's disease (Byun, PLoS One 2012), and traumatic brain injury (The SAFE Study Investigators, N Engl J Med 2007). Reducing circulating albumin may also be useful in the treatment of diabetes mellitus, end stage kidney failure, and other illnesses, diseases, or disorders.

FcRn, also known as the neonatal Fc receptor, is an integral membrane Fc receptor for albumin FcRn is a heterodimer of a membrane bound alpha-chain (GenBank accession no. NM004107) and soluble β2-microglobulin (β2m) (GenBank accession no. NM004048) and is structurally related to MHC class I molecules. FcRn regulates albumin concentrations by binding to and protecting endocytosed albumin from degradation in the lysosomal compartment, and transporting the albumin to the cell surface for release at neutral extracellular pH. Through this mechanism, FcRn is responsible for the long serum half-life of albumin. Accordingly, specific blockade of FcRn-albumin interaction can be used to promote degradation of pathogenic albumin-bound toxins.

Provided are antibodies that are derived from a murine antibody which specifically binds to FcRn and blocks binding of FcRn to albumin but does not substantially bind to the IgG-Fc binding site of FcRn. The antibodies have substantial improvements in binding affinity for FcRn at pH 7.4 and pH 6.0, and thus block binding of albumin to FcRn under physiologic and acidic conditions. The antibodies are useful in the treatment of autoimmune and inflammatory diseases. The antibodies comprise one or more affinity matured CDRs. The affinity maturation procedure provides antibodies that bind with high affinity to FcRn over the critical pH range 6.0 to 7.4. Thus, the antibodies effectively block binding of albumin once internalized into the acidic environment of the endosome.

According to certain embodiments, the improved antibodies also feature humanized frameworks for reduced immunogenicity. In certain embodiments, CDRs of an FcRn-specific antibody are located in frameworks obtained from a human antibody. In other embodiments, CDRs of an FcRn-specific antibody are located in frameworks that are a composite of two or more human antibodies. In other embodiments, surface-exposed framework residues of an FcRn-specific antibody are replaced with framework residues of a human antibody. In a preferred embodiment, the frameworks are selected to minimize the presence of amino acid sequences predicted to be T cell epitopes over a wide population range. The CDRs may also be located in murine frameworks linked to human constant regions (i.e., chimeric antibodies).

As described further herein, for affinity maturation the heavy chain variable domain CDR3 regions were mutated and screened in scFv form at pH 6.0 and pH 7.4 Amino acid sequence variation was introduced into the heavy chain CDR3H region at amino acid positions 94-100 (a.a. 95-100 of CDR3H and a.a. 94 of FW3) using an oligonucleotide comprising the sequence ARGBNSVVSBNCVNCN-VCRSC (SEQ ID NO:41) which provided for selected amino acids at each position as follows: a.a. 94: K, R; a.a. 95: A, C, D, E, F, G, H, I, L, P, Q, R, S, V, W, Y; a.a. 96: A, D, E, G, H, K, N, P, Q, R, S, T; a.a. 97: A, C, D, F, G, H, L, P, R, S, T, V, Y; a.a. 98: A, D, G, H, I, L, N, P, R, S, T, V; a.a. 99: A, C, D, G, H, N, P, R, S, T, Y; a.a. 100: A, G, S, T Amino acid sequence variation was introduced into the heavy chain CDR3H region at amino acid positions 94-99 (a.a. 95-99 of CDR3H and a.a. 94 of FW3) using an oligonucleotide comprising the sequence AGGNNSNNSNNSNNSRSC (SEQ ID NO:42) which provided for selected amino acids at each position as follows: a.a. 94: R; a.a. 95: A, C, D, E, F, G, H, I, K, L, M, N, P, Q, R, S, T, V, W, Y; a.a. 96: A, C, D, E, F, G, H, I, K, L, M, N, P, Q, R, S, T, V, W, Y; a.a. 97: A, C, D, E, F, G, H, I, K, L, M, N, P, Q, R, S, T, V, W, Y; a.a. 98: A, C, D, E, F, G, H, I, K, L, M, N, P, Q, R, S, T, V, W, Y; a.a. 99: A, G, S, T.

As shown in the Examples below, this led to several CDR3H variants that conferred substantial improvements in FcRn binding affinity. Inspection of the variants obtained compared to the variability introduced into the CDR3H library indicates certain positions where amino acids remained relatively unchanged and others where variation could be introduced and result in improved binding. Accordingly, provided is an antibody or binding portion thereof that binds to FcRn, wherein the heavy chain comprises CDR3H, comprising certain amino acids that can be varied. In one such embodiment, CDR3H comprises $X_1ESTTX_2$, wherein $X_1$ is A, or L; and $X_2$ is T, or R; (SEQ ID NO:43). In another such embodiment, the heavy chain CDR3H is $X_1ESTTX_2VGDY$, wherein $X_1$ is A, or L; and $X_2$ is T, or R (SEQ ID NO:44). In another such embodiment, the heavy chain CDR3H comprises $X_1ESTTX_2$, wherein $X_1$ is G, A, or L; and $X_2$ is T, or R (SEQ ID NO:45). In another such embodiment, the heavy chain CDR3H is $X_1ESTTX_2VGDY$, wherein $X_1$ is G, A, or L; and $X_2$ is T, or R (SEQ ID NO:46). In another such embodiment, the heavy chain CDR3H comprises $X_1X_2X_3X_4X_5 X_6$, wherein $X_1$ is G, A, F, or L; $X_2$ is E, A, or D; $X_3$ is S, T, or A; $X_4$ is T, L, P, or V; $X_5$ is T, S, or A; and $X_6$ is T or A (SEQ ID NO:47). In another such embodiment, the heavy chain CDR3H is $X_1X_2X_3X_4X_5 X_6VGDY$, wherein $X_1$ is G, A, F, or L; $X_2$ is E, A, or D; $X_3$ is S, T, or A; $X_4$ is T, L, P, or V; $X_5$ is T, S, or A; and $X_6$ is T or A (SEQ ID NO:48).

In certain embodiments, CDR3H is GESTTTVGDY (SEQ ID NO:25), AESTTTVGDY (SEQ ID NO:27), FSSLSTVGDY (SEQ ID NO:29), or LESTTAVGDY (SEQ ID NO:31). In certain embodiments, CDR3H is FDTPATVGDY (SEQ ID NO:33), FDTPSTVGDY (SEQ ID NO:35), FDSLSTVGDY (SEQ ID NO:37), or LEAVSAVGDY (SEQ ID NO:39). In certain of these embodiments, the amino acid at position 103 of the heavy chain variable domain is tryptophan. In certain of these embodiments, the amino acid at position 103 of the heavy chain variable domain is arginine.

In certain embodiments wherein CDR3H is as set forth above, CDR1H is set forth by SEQ ID NO:2, and CDR2H set forth by SEQ ID NO:4.

Several heavy and light chain frameworks were developed. The humanized frameworks were assembled from human variable domain sequences, with an eye to minimizing immunogenic T cell epitopes. Three such humanized heavy chain frameworks and four such light chain humanized frameworks are exemplified: $V_H1$ (SEQ ID NO:12); $V_H3$ (SEQ ID NO:14); $V_H4$ (SEQ ID NO:16); Vκ1 (SEQ ID NO:18); Vκ2 (SEQ ID NO:20); Vκ3 (SEQ ID NO:22); and Vκ4 (SEQ ID NO:24). Corresponding oligonucleotide sequences for these exemplified humanized frameworks are set forth by: SEQ ID NO:11 ($V_H1$); SEQ ID NO:13 ($V_H3$); SEQ ID NO:15 ($V_H4$); SEQ ID NO:17 (Vκ1); SEQ ID NO:19 (Vκ2); SEQ ID NO:21 (Vκ3); and SEQ ID NO:23 (Vκ4). In the heavy chain variable domain sequences provided in SEQ ID NO:12, SEQ ID NO:14, SEQ ID NO:16, and SEQ ID NO:18, CDR1H, CDR2H, and CDR3H amino acids are represented as "Xaa." The amino acid sequences of CDR1H and CDR2H are as set forth in SEQ ID NO:2 and SEQ ID NO: 4, respectively. A corresponding oligonucleotide sequence for CDR1H is set forth by SEQ ID NO:1 and a corresponding oligonucleotide sequence for CDR2H is set forth by SEQ ID NO:3. In the light chain variable domain sequences provided in SEQ ID NO:18, SEQ ID NO:20, SEQ ID NO:22, and SEQ ID NO:24, a particular amino acid is specified at all positions. The amino acid sequences of CDR1L is as set forth in SEQ ID NO:6, CDR2L as set forth in SEQ ID NO:8, and CDR3L as set forth in SEQ ID NO:10. Corresponding oligonucleotide sequences are as set forth by: SEQ ID NO:5 (CDR1L); SEQ ID NO:7 (CDR2L); and SEQ ID NO:9 (CDR3L). The locations of FWs and CDRs in the heavy and light chains will also be evident from FIG. 1 and FIG. 2, respectively.

Table 1 provides non-limiting examples of affinity matured, humanized FcRn-binding antibody heavy and light chain variable domains and CDRs. As describe herein, the variable domains were selected for improved binding at pH 6.0 and pH 7.4, and demonstrate substantially improved binding relative to the parent murine antibody.

TABLE 1

Antibody Amino Acid Sequences by SEQ ID NO

|  | CDR1H | CDR2H | CDR3H | $V_H$ |
| --- | --- | --- | --- | --- |
| G15_C3 $V_H1$ | 2 | 4 | 25 | 26 |
| G47_B10 $V_H1$ | 2 | 4 | 27 | 28 |
| G47_H6 $V_H1$ | 2 | 4 | 29 | 30 |
| G50_C10 $V_H1$ | 2 | 4 | 31 | 32 |
| G54_D11 $V_H1$ | 2 | 4 | 33 | 34 |
| G52_G9 $V_H1$ | 2 | 4 | 35 | 36 |
| G49_H9.3 $V_H1$ | 2 | 4 | 37 | 38 |
| G49_H9.5 $V_H1$ | 2 | 4 | 39 | 40 |

The affinity matured heavy chain CDR3s may be combined with a heavy chain CDR1 (e.g., a CDR1 having SEQ ID NO:2) and/or a heavy chain CDR2 (e.g., a CDR2 having SEQ ID NO:4).

As disclosed in the Examples below, various antibody variable domains exemplified herein are based on a murine antibody and contain affinity matured CDRs, and certain embodiments also feature humanized FWs. Any heavy chain variable domain disclosed in Table 1 may be coexpressed with any disclosed light chain to create a functional anti-FcRn antibody. Moreover, an affinity matured heavy chain variable domain may be paired with a humanized non-affinity matured light chain variable domain disclosed herein, and an affinity matured light chain variable domain may be paired with a humanized non-affinity matured heavy chain variable domain. In a preferred embodiment, an affinity matured heavy chain variable domain may be paired with a humanized light chain variable domain. Also, Table 1 sets forth heavy chain CDRs in $V_H1$. The heavy chain CDRs are also compatible with, e.g., frameworks $V_H3$, and $V_H4$ disclosed herein (see FIG. 1). As used herein, the designations $V_H1$, $V_H3$, $V_H4$, Vκ1, Vκ2, Vκ3, and Vκ4 refer to exemplary humanized frameworks disclosed herein, and are not references to human germline gene families. It will be apparent that any heavy chain or light chain variable domain disclosed herein can be combined with a library of complementary variable domains and screened to identify new antibodies having improved or altered binding characteristics.

Provided herein are antibodies and antigen binding portions that are similar, but not identical to, those disclosed in Table 1. The antibodies can have one or more amino acid substitutions, deletions, insertions, and/or additions. In certain embodiments, an FcRn antibody comprises a heavy chain variable domain that is at least 85%, at least 90%, or at least 95% identical to a heavy chain variable domain set forth in Table 1.

In an embodiment, an FcRn antibody contains a heavy chain variable domain which comprises CDR sequences, i.e., CDR1H, CDR2H, and CDR3H, set forth in Table 1 and a framework (i.e., FW1, FW3, and FW4) of $V_H1$, $V_H3$, or $V_H4$ or a framework that is at least 85%, 90%, or 95% identical to a framework of $V_H1$, $V_H3$, or $V_H4$. In an embodiment, an FcRn antibody contains a heavy chain variable domain which comprises CDR sequences set forth in Table 1 and frameworks such that the heavy chain variable domain sequence is at least 85%, or at least 90%, or at least 95% identical to a variable domain set forth in Table 1.

In an embodiment, an FcRn antibody contains a heavy chain variable domain which comprises CDR sequences, i.e., CDR1H, CDR2H, and CDR3H, set forth in Table 1 and a framework (i.e., FW1, FW3, and FW4) of $V_H1$, $V_H3$, or $V_H4$ or a framework that is at least 85%, 90%, or 95% identical to a framework of $V_H1$, $V_H3$, or $V_H4$, and a light chain variable domain which comprises Vκ1, Vκ2, Vκ3, or Vκ4 or a sequence that is at least 85%, 90%, or 95% identical to Vκ1, Vκ2, Vκ3, or Vκ4.

"Identity" refers to the number or percentage of identical positions shared by two amino acid or nucleic acid sequences, taking into account the number of gaps, and the length of each gap, which need to be introduced for optimal alignment of the two sequences.

Where an amino acid sequence is described as being at least 85%, or at least 90%, or at least 95% identical to another amino acid sequence, the amino acid sequences may differ by conservative substitutions (including where all substitutions are conservative substitutions).

Amino acid substitutions can be made, in some cases, by selecting substitutions that do not differ significantly in their effect on maintaining (a) the structure of the peptide backbone in the area of the substitution, (b) the charge or hydrophobicity of the molecule at the target sit; or (c) the bulk of the side chain. For example, naturally occurring residues can be divided into groups based on side-chain properties; (1) hydrophobic amino acids (methionine, alanine, valine, leucine, and isoleucine); (2) neutral hydrophilic amino acids (cysteine, serine, and threonine); (3) acidic amino acids (aspartic acid and glutamic acid); (4) basic amino acids (asparagine, glutamine, histidine, lysine, and arginine); (5) amino acids that influence chain orientation (glycine and proline); and (6) aromatic amino acids (tryptophan, tyrosine, and phenylalanine). Substitutions made within these groups can be considered conservative substitutions. Examples of substitutions include, without limitation, substitution of valine for alanine, lysine for arginine, glutamine for asparagine, glutamic acid for aspartic acid, serine for cysteine, asparagine for glutamine, aspartic acid for glutamic acid, proline for glycine, arginine for histidine, leucine for isoleucine, isoleucine for leucine, arginine for lysine, leucine for methionine, leucine for phenylalanine, glycine for proline, threonine for serine, serine for threonine, tyrosine for tryptophan, phenylalanine for tyrosine, and/or leucine for valine.

Methods and computer programs for determining sequence similarity are publicly available, including, but not limited to, the GCG program package (Devereux et al., Nucleic Acids Research 12: 387, 1984), BLASTP, BLASTN, FASTA (Altschul et al., J. Mol. Biol. 215:403 (1990), and the ALIGN program (version 2.0). The well-known Smith Waterman algorithm may also be used to determine similarity. The BLAST program is publicly available from NCBI and other sources (BLAST Manual, Altschul, et al., NCBI NLM NIH, Bethesda, Md. 20894; BLAST 2.0 at http://www.ncbi.nlm nih.gov/blast/). In comparing sequences, these methods account for various substitutions, deletions, and other modifications.

As used herein, the term "Complementarity Determining Regions" (CDRs, i.e., CDR1, CDR2, and CDR3) refers to the amino acid residues of an antibody variable domain the presence of which are necessary for antigen binding. Each variable domain typically has three CDR regions identified as CDR1, CDR2 and CDR3. Each complementarity determining region can comprise amino acid residues from a "complementarity determining region" as defined by Kabat (i.e., about residues 24-34 (L1), 50-56 (L2) and 89-97 (L3) in the light chain variable domain and 31-35 (H1), 50-65 (H2) and 95-102 (H3) in the heavy chain variable domain. Likewise, "frameworks" (FWs) comprise amino acids 1-23 (FW1), 35-49 (FW2), 57-88 (FW3), and 98-107 (FW4) in the light chain variable domain and 1-30 (FW1), 36-49 (FW2), 66-94 (FW3), and 103-113 (FW4) in the heavy chain variable domain taking into account the Kabat numbering system (Kabat et al., Sequences of Proteins of Immunological Interest, 5th Ed. Public Health Service, National Institutes of Health, Bethesda, Md. (1987, 1991)).

The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence.

As used herein, "antibody variable domain" refers to the portions of the light and heavy chains of antibody molecules that include amino acid sequences of Complementarity Determining Regions (CDRs; i.e., CDR1, CDR2, and CDR3), and Framework Regions (FRs). $V_H$ refers to the variable domain of the heavy chain. $V_L$ refers to the variable domain of the light chain.

Antibodies are proteins that recognize and bind to a specific antigen or substance. In preferred embodiments, the antibodies or antigen-binding portions set forth herein bind FcRn at least as strongly as the natural ligand (i.e., albumin). Affinity, represented by the equilibrium constant for the dissociation of an antigen with an antibody (Kd), measures the binding strength between an antigenic determinant and an antibody binding site. The affinity of an antibody for an antigen may be determined by the use of a suitable surface plasmon energy resonance measurement. Such a measurement might be the BIACORE® assay described in International Patent Application Publication WO 2005/012359 and elsewhere herein. Other methods of determining affinity include enzyme-linked immunosorbent assays or competition assays such as radioimmunoassays.

Avidity is the measure of the strength of binding between an antibody with its antigen. Avidity is related to both the affinity between an antigenic determinant and an antigen binding site on the antibody, and the number of binding sites (valence) per antibody. For example, a monovalent antibody (e.g., Fab or scFv) has one binding site for a particular epitope. An IgG antibody has two antigen binding sites. Typical values of K (the reciprocal of the dissociation constant $K_d$) are $10^5$ to $10^{11}$ liters/mol. Any K weaker than $10^4$ liters/mol is considered to indicate binding which is nonspecific.

In certain embodiments, the antibodies or antigen-binding portions thereof described herein bind to the albumin-binding portion of human FcRn with a $K_d$ of $10^5$ to $10^{12}$ liters/mol, $10^6$ to $10^{12}$ liters/mol, $10^7$ to $10^{12}$ liters/mol, $10^8$ to $10^{12}$ liters/mol, $10^9$ to $10^{12}$ liters/mol, $10^{10}$ to $10^{12}$ liters/mol, or $10^{11}$ to $10^{12}$ liters/mol. In other embodiments, the antibodies or antigen-binding portions thereof described herein bind to the albumin-binding portion of human FcRn with a $K_d$ of $10^5$ to $10^{11}$ liters/mol, $10^6$ to $10^{11}$ liters/mol, $10^7$ to $10^{11}$ liters/mol, $10^8$ to $10^{11}$ liters/mol, $10^9$ to $10^{11}$ liters/mol, or $10^{10}$ to $10^{11}$ liters/mol. In other embodiments, the antibodies or antigen-binding portions thereof described herein bind to the albumin-binding portion of human FcRn with a $K_d$ of $10^5$ to $10^{10}$ liters/mol, $10^6$ to $10^{10}$ liters/mol, $10^7$ to $10^{10}$ liters/mol, $10^8$ to $10^{10}$ liters/mol, or $10^9$ to $10^{10}$ liters/mol. In other embodiments, the antibodies or antigen-binding portions thereof described herein bind to the albumin-binding portion of human FcRn with a $K_d$ of $10^5$ to $10^8$ liters/mol, $10^6$ to $10^8$ liters/mol, or $10^7$ to $10^8$ liters/mol.

In order to minimize immunogenicity when administered to a human, the antibodies or antigen-binding portions thereof set forth herein preferably include human constant domains. Thus, the antibodies can be any isotype or subtype, including but not limited to $IgG_1$, $IgG_{2a}$, $IgG_{2b}$, $IgG_3$, $IgG_4$, IgM, IgA, IgD, or IgE. The antibody class may be selected to optimize effector functions (e.g., to increase or reduce complement dependent cytotoxicity (CDC) or antibody dependent cellular cytotoxicity (ADCC)). In certain embodiments, the constant region (i.e., $C_H1$, $C_H2$, $C_H3$, and/or the hinge region) is modified, for example to increase or decrease binding to an Fc receptor. In certain embodiments, the constant domain is modified to promote or stabilize heavy chain-heavy chain binding. In certain embodiments, the antibody is an $IgG_4$ antibody and the hinge region of the heavy chains is modified by changing the serine at position 241 to proline, leading to extended serum half-life (Angal et al., 1993, Mol. Immunol. 30:105-108). In certain embodiments, the antibody is an $IgG_4$ antibody and the C-terminal lysines at position 478 of the heavy chains are deleted. In some embodiments, the IgG4 antibody has both the S241P modifications and lacks the C-terminal lysines.

In certain embodiments, FcRn-binding antibody fragments are provided. An Fv is the smallest fragment that contains a complete heavy and light chain variable domain, including all six hypervariable loops (CDRs). Lacking constant domains, the variable domains are noncovalently associated. The heavy and light chains may be connected into a single polypeptide chain (a "single-chain Fv" or "scFv") using a linker that allows the $V_H$ and $V_L$ domains to associate to form an antigen binding site. See, e.g., Bird et al., 1988, Science 242:423 and Huston et al, 1988, Proc. Natl. Acad. Sci. USA 85:5879. In an embodiment, the linker is (Gly-Gly-Gly-Gly-Ser)$_3$. Since scFv fragments lack the constant domains of whole antibodies, they are considerably smaller than whole antibodies. scFv fragments are also free of normal heavy-chain constant domain interactions with other biological molecules which may be desired in certain embodiments.

"Antibodies," as used herein, refers to monomers as well as multimers and binding fragments. Intact antibodies, including multimers, or antibody fragments bearing antigen-binding regions of antibodies can be used. Antigen-binding regions include, without limitation, Fv, scFv, Fab, Fab' and F(ab')$_2$ fragments. Methods for preparing antibody fragments are well known in the art. For example, monovalent Fab fragments, which lack the heavy chain hinge region can be prepared from whole immunoglobulin by proteolytic digestion with papain. Bivalent F(ab')2 fragments, which retain the heavy chain hinge region can be prepared by proteolytic digestion with pepsin.

Fragments of an antibody containing $V_H$, $V_L$, and optionally CL, $C_H1$, or other constant domains can also be used. Such fragments may also be recombinantly produced. Many other useful antigen-binding antibody fragments are known in the art, and include, without limitation, diabodies, triabodies, single domain antibodies, and other monovalent and multivalent forms.

Further provided are multivalent antigen-binding proteins, which can be in the form, without limitation, of antibodies, antigen-binding fragments thereof, and proteins comprising all or part of antigen-binding portions of antibodies. Multivalent antigen-binding proteins may be monospecific, bispecific, or multispecific. The term specificity refers to the number of different types of antigenic determinants to which a particular molecule can bind. If an immunoglobulin molecule binds to only one type of antigenic determinant, the immunoglobulin molecule is monospecific. If the immunoglobulin molecule binds to different types of antigenic determinants then the immunoglobulin molecule is multispecific.

In one embodiment, a multivalent single chain antibody includes a variable light-chain fragment linked to a variable heavy-chain fragment (similar to an scFv), which is further linked by another peptide linker to at least one other antigen binding domain. Typically, the peptide linker is composed of about fifteen amino acid residues. In a preferred embodiment, the number of $V_L$ and $V_H$ domains is equivalent. For example, a bivalent single chain antibody can be represented as follows: $V_L$-$L_1$-$V_H$-$L_2$-$V_L$-$L_3$-$V_H$ or $V_L$-$L_1$-$V_H$-$L_2$-$V_H$-$L_3$-$V_L$ or $V_H$-$L_1$-$V_L$-$L_2$-$V_H$-$L_3$-$V_L$ or $V_H$-$L_1$-$V_L$-$L_2$-$V_L$-$L_3$-$V_H$. Multivalent single chain antibodies which are trivalent or greater have one or more antibody fragments joined to a bivalent single chain antibody by additional peptide linkers. One example of a trivalent single chain antibody is: $V_L$-$L_1$-$V_H$-$L_2$-$V_L$-$L_r$-$V_H$-$L_2$-$V_L$$L_r$-$V_H$.

Two single chain antibodies can be combined to form a diabody, also known as bivalent dimer. See, e.g., European Patent Application 0 404 097 or Hollinger et al., 1993, Proc. Natl. Acad. Sci. USA 90:6444. Diabodies have two chains. Each chain of the diabody includes a $V_H$ domain connected to a $V_L$ domain by a short linker of about 5-10 amino acid residues, e.g., (Gly-Gly-Gly-Gly-Ser), (Gly-Gly-Gly-Gly-Ser)$_2$. Such linkers are short enough to prevent intrachain pairing between domains on the same chain, thus driving interchain pairing between complementary domains on different chains and recreate two antigen-binding sites. The diabody structure is compact, with antigen-binding sites at opposite ends of the molecule.

$V_H$ and $V_L$ framework sequence variants and affinity matured antibodies can be subjected to a pre-clinical ex vivo assay to assess potential immunogenicity. One such assay is EPISCREEN™ which provides an effective technology for predicting T cell immunogenicity by quantifying T cell responses to protein therapeutics. The assay uses a cohort of blood donors carefully selected based on MHC class II haplotypes to best represent the number and frequency of HLA-DR allotypes expressed in the world population. The assay provides a method by which the immunogenicity of whole proteins can be assessed both in terms of magnitude and frequency of T cell responses (Jones et al., J Interferon Cytokine Res. 2004 24(9):560-72; Jones et al., J Thromb Haemost. 2005 3(5):991-1000).

Antibodies which compete with or cross-block the binding of an antibody disclosed herein to FcRn, or which themselves are cross-blocked from binding FcRn by an antibody disclosed herein, may be used in the methods of blocking FcRn activity disclosed herein. In some cases, these competing, cross-blocking, or cross-blocked antibodies bind to an epitope of FcRn which borders and/or overlaps with the epitope bound by an antibody described herein. In some cases, these competing, cross-blocking, or cross-blocked antibodies are chimeric, fully human, or humanized antibodies that bind to an epitope of FcRn which is the same as the epitope bound by an antibody described herein.

Competing, cross-blocking, and cross-blocked antibodies can be identified using any suitable method known in the art, including competition ELISAs or BIACORE® assays where binding of the competing or cross blocking antibody to human FcRn prevents the binding of an antibody disclosed herein or vice versa.

In certain embodiments, the competing or cross-blocking antibody is an antibody which blocks the binding of albumin to human FcRn and which competes with or cross-blocks the binding of an antibody having a heavy chain sequence selected from the group consisting of SEQ ID NO:26, SEQ ID NO:28, SEQ ID NO:30, SEQ ID NO:32, SEQ ID NO:34, SEQ ID NO:36, SEQ ID NO:38, and SEQ ID NO:40, and a light chain sequence selected from the group consisting of SEQ ID NO:18, SEQ ID NO:20, SEQ ID NO:22, and SEQ ID NO:24. In some embodiments, the competition or cross-blocking is greater than 80%, greater than 85%, greater than 90%, or greater than 95%.

In certain embodiments, the competing or cross-blocking antibody is an antibody which blocks the binding of albumin to human FcRn and which competes with or cross-blocks the binding of an antibody having a heavy chain sequence of SEQ ID NO:28 and a light chain sequence of SEQ ID NO:22. In some embodiments, the competition or cross-blocking is greater than 80%, greater than 85%, greater than 90%, or greater than 95%.

In certain embodiments, the competing or cross-blocking antibody is an antibody which blocks the binding of albumin to human FcRn and which competes with or cross-blocks the binding of an antibody having a heavy chain sequence of SEQ ID NO:32 and a light chain sequence of SEQ ID NO:22. In some embodiments, the competition or cross-blocking is greater than 80%, greater than 85%, greater than 90%, or greater than 95%.

In certain embodiments, the competing or cross-blocked antibody is an antibody which blocks the binding of albumin to human FcRn and whose binding to FcRn is competed with or cross-blocked by an antibody having a heavy chain sequence selected from the group consisting of SEQ ID NO:26, SEQ ID NO:28, SEQ ID NO:30, SEQ ID NO:32, SEQ ID NO:34, SEQ ID NO:36, SEQ ID NO:38, and SEQ ID NO:40, and a light chain sequence selected from the group consisting of SEQ ID NO:18, SEQ ID NO:20, SEQ ID NO:22, and SEQ ID NO:24. In some embodiments, the competing or cross-blocked antibody is competed with or cross-blocked to greater than 80%, greater than 85%, greater than 90%, or greater than 95%.

In certain embodiments, the competing or cross-blocked antibody is an antibody which blocks the binding of albumin to human FcRn and whose binding to FcRn is competed with or cross-blocked by an antibody having a heavy chain sequence of SEQ ID NO:28 and a light chain sequence of SEQ ID NO:22. In some embodiments, the competing or cross-blocked antibody is competed with or cross-blocked to greater than 80%, greater than 85%, greater than 90%, or greater than 95%.

In certain embodiments, the competing or cross-blocked antibody is an antibody which blocks the binding of albumin to human FcRn and whose binding to FcRn is competed with or cross-blocked by an antibody having a heavy chain sequence of SEQ ID NO:32 and a light chain sequence of SEQ ID NO:22. In some embodiments, the competing or cross-blocked antibody is competed with or cross-blocked to greater than 80%, greater than 85%, greater than 90%, or greater than 95%.

In some embodiments, the competing, cross-blocking, or cross-blocked antibodies are chimeric, fully human, or are humanized. In some embodiments, the competing, cross-blocking, or cross-blocked antibodies bind to the albumin-binding site of human FcRn with an affinity of $10^5$ to $10^{11}$ liters/mol., $10^6$ to $10^{11}$ liters/mol., $10^7$ to $10^{11}$ liters/mol., $10^8$ to $10^{11}$ liters/mol., $10^9$ to $10^{11}$ liters/mol., or $10^{10}$ to $10^{11}$ liters/mol.

Also provided herein are nucleic acids encoding anti-FcRn antibodies and functional fragments thereof, vectors, host cells and expression systems. The nucleic acids encoding anti-FcRn antibodies and functional fragments thereof may be, e.g., DNA, cDNA, RNA, synthetically produced DNA or RNA, or a recombinantly produced chimeric nucleic acid molecule comprising any of those polynucleotides either alone or in combination. For example, provided is an expression vectors containing a polynucleotide sequence encoding an anti-FcRn antibodies described herein operably linked to expression control sequences suitable for expression in a eukaryotic and/or prokaryotic host cell. A variety of expression vectors have been developed for the efficient synthesis of antibodies and fragments in prokaryotic cells such as bacteria and eukaryotic systems, including but not limited to yeast and mammalian cell culture systems have been developed. The vectors can comprise segments of chromosomal, non-chromosomal and synthetic DNA sequences. In some embodiments, the nucleic acids may comprise SEQ ID NO:1, SEQ ID NO:3, SEQ ID NO:5, SEQ ID NO:6, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:41, or SEQ ID NO:42.

Any suitable expression vector can be used. For example, prokaryotic cloning vectors include plasmids from *E. coli*, such as colE1, pCR1, pBR322, pMB9, pUC, pKSM, and RP4. Prokaryotic vectors also include derivatives of phage DNA such as M13 and other filamentous single-stranded DNA phages. An example of a vector useful in yeast is the 2µ plasmid. Suitable vectors for expression in mammalian cells include well-known derivatives of SV40, adenovirus, retrovirus-derived DNA sequences and shuttle vectors derived from combination of functional mammalian vectors, such as those described above, and functional plasmids, e.g., pLenti6.3/V5-DEST®, pT-Rex™-DEST31®, pGene/V5-HispGene/V5-His® (Life Technologies, Norwalk, Conn.).

Additional eukaryotic expression vectors are known in the art (e.g., P. J. Southern and P. Berg, J. Mol. Appl. Genet., 1, 327-341 (1982); Subramani et al., Mol. Cell. Biol., 1: 854-864 (1981); Kaufmann and Sharp, "Amplification And Expression of Sequences Cotransfected with a Modular Dihydrofolate Reductase Complementary DNA Gene," J. Mol. Biol. 159, 601-621 (1982); Kaufmann and Sharp, Mol. Cell. Biol. 159, 601-664 (1982); Scahill et al., "Expression And Characterization Of The Product Of A Human Immune Interferon DNA Gene In Chinese Hamster Ovary Cells," Proc. Nat'l Acad. Sci. USA 80, 4654-4659 (1983); Urlaub and Chasin, Proc. Nat'l Acad. Sci. USA 77, 4216-4220, (1980).

The expression vectors may contain at least one expression control sequence that is operatively linked to the DNA sequence or fragment to be expressed. The control sequence is inserted in the vector in order to control and to regulate the expression of the cloned DNA sequence. Examples of useful expression control sequences are the lac system, the trp system, the tac system, the trc system, major operator and promoter regions of phage lambda, the control region of fd coat protein, the glycolytic promoters of yeast, e.g., the promoter for 3-phosphoglycerate kinase, the promoters of yeast acid phosphatase, e.g., PhoS, the promoters of the yeast alpha-mating factors, and promoters derived from cytomegalovirus, polyoma, adenovirus, retrovirus, and simian virus, e.g., the early and late promoters or SV40, and other sequences known to control the expression of genes of prokaryotic or eukaryotic cells and their viruses or combinations thereof. Other expression control sequences that may be used include DNA regulatory sequences from the Chinese hamster elongation factor-1α (CHEF1) gene (Running Deer & Allison, 2004, Biotechnol. Prog. 20:880-889; U.S. Pat. No. 5,888,809).

Also provided are recombinant host cells containing the expression vectors previously described. Antibodies or antigen-binding portions thereof set forth herein can be expressed in cell lines other than in hybridomas. Nucleic acids, which comprise a sequence encoding a polypeptide as described herein, can be used for transformation of a suitable mammalian host cell.

Cell lines of particular preference are selected based on high level of expression, constitutive expression of protein of interest and minimal contamination from host proteins. Mammalian cell lines available as hosts for expression are well known in the art and include many immortalized cell lines, such as but not limited to, NS0 cells, Chinese Hamster Ovary (CHO) cells, Baby Hamster Kidney (BHK) cells and many others. In some embodiments, the cell is a myeloma cell, e.g., SP2/0, which can be transfected and grown in culture of in the peritoneal cavity of a mouse where high concentrations of IgG can be recovered from ascites fluid. Suitable additional eukaryotic cells include yeast and other fungi. Useful prokaryotic hosts include, for example, *E. coli*, such as *E. coli* SG-936, *E. coli* HB 101, *E. coli* W3110, *E. coli* X1776, *E. coli* X2282, *E. coli* DHI, and *E. coli* MRCl, *Pseudomonas*, *Bacillus*, such as *Bacillus subtilis*, and *Streptomyces*.

These present recombinant host cells can be used to produce an antibody, or antigen-binding portion thereof, by culturing the cells under conditions permitting expression of the antibody or fragment thereof and purifying the antibody or fragment thereof from the host cell or medium surrounding the host cell. Thus, in one embodiment, provided is a method for the production of an antibody capable of binding the albumin-binding region of FcRn, said method comprising: (a) culturing a host cell as described above; and (b) isolating said antibody from the host cell or the culture medium of the host cell.

The transformed hosts can be grown in fermentors and cultured according to techniques known in the art. Once the desired level of expression of the antibodies is reached, the antibodies can be purified according to standard procedures of the art, including ammonium sulfate precipitation, purification on affinity columns, column chromatography, gel electrophoresis and the like. For use in the therapeutic methods described herein, it is preferred that the antibodies be purified to at least 90%, 95%, 98%, or 99% purity.

Targeting of the expressed antibody or fragment for secretion in the recombinant host cells can be facilitated by inserting a signal or secretory leader peptide-encoding sequence (see, Shokri et al., Appl Microbiol Biotechnol. 60(6):654-64 (2003), Nielsen et al., Prot. Eng. 10:1-6 (1997) and von Heinje et al., Nucl. Acids Res. 14:4683-4690 (1986)) at the 5' end of the antibody-encoding gene of interest. These secretory leader peptide elements can be derived from either prokaryotic or eukaryotic sequences. Accordingly suitably, secretory leader peptides are used, being amino acids joined to the N-terminal end of a polypeptide to direct movement of the polypeptide out of the host cell cytosol and secretion into the medium.

The antibodies or antigen-binding portions thereof can be fused to additional amino acid residues. Such amino acid residues can be a peptide tag, perhaps to facilitate isolation. Other amino acid residues for homing of the antibodies to specific organs or tissues are also contemplated.

In some embodiments, the antibody or antigen-binding portion thereof is conjugated to one or more effector molecules, which provide some desirable property (e.g., increased serum half-life) to the antibody or antigen-binding portion thereof. In a particular embodiment, the antibody or antigen-binding portion thereof is conjugated to polyethyleneglycol (PEG). The PEG may be attached to any amino acid side chain or terminal amino acid functional group, e.g., a free amino, imino, thiol, hydroxyl, or carboxyl group. Methods of attaching PEG to antibodies are known in the art and may be employed. See, e.g., European Patent Application EP 0948544; European Patent Application EP1090037; "Poly(ethyleneglycol) Chemistry, Biotechnical and Biomedical Applications," 1992, J. Milton Harris (ed), Plenum Press, New York; "Poly(ethyleneglycol) Chemistry and Biological Applications," 1997, J. Milton Harris & S. Zalipsky (eds), American Chemical Society, Washington D.C.; "Bioconjugation Protein Coupling Techniques for the Biomedical Sciences," 1998, M. Aslam & A. Dent, Grove Publishers, New York; or Chapman, A. 2002, Advanced Drug Delivery Reviews 2002, 54:531-545.

In another embodiment, an antibody or antigen-binding portion thereof as set forth herein is made by expressing a nucleic acid encoding the antibody in a transgenic animal, such that the antibody is expressed and can be recovered. For example, the antibody can be expressed in a tissue specific manner that facilitates recovery and purification. In one such embodiment, an antibody of the expressed in the mammary gland for secretion during lactation. Transgenic animals, include but are not limited to mice, goat, and rabbit.

Provided herein are methods of identifying antibodies that bind FcRn at both acidic pH and physiological pH and also bind at an epitope that competes with albumin binding to FcRn. The methods comprise two or more screening steps that are carried out at acidic pH (e.g., pH 5.0-6.6, pH 5.8-6.4, pH 6.0-6.2, or pH 6.0). The two or more acidic screening steps are alternated with screening steps carried out at physiological pH (e.g., pH 6.8-8.2, pH 6.8-7.6, pH 7.2-7.4, or pH 7.4).

For example, one embodiment of such methods comprises:
(a) contacting a collection of candidate antibodies with FcRn or a portion thereof at pH 5.8-6.4 and isolating the antibodies that bind to FcRn or a portion thereof;
(b) contacting the isolated antibodies of step (a) with FcRn or a portion thereof at pH 6.8-7.6 and isolating the antibodies that bind to FcRn or a portion thereof;
(c) contacting the isolated antibodies of step (b) with FcRn or a portion thereof at pH 5.8-6.4 and isolating the antibodies that bind to FcRn or a portion thereof.
(d) assaying the isolated antibodies of step (c) for ability to block albumin binding to FcRn.

Another embodiment comprises:
(a) providing a collection of candidate FcRn-binding antibodies:
(b) contacting the collection of candidate FcRn-binding antibodies with FcRn or a portion thereof at pH 6.0 under conditions such that complexes are formed between the FcRn or a portion thereof and at least some of the candidate FcRn-binding antibodies;
(c) isolating the complexes;
(d) separating the candidate FcRn-binding antibodies from the isolated complexes;
(e) contacting the separated candidate FcRn-binding antibodies from step (d) with FcRn or a portion thereof at pH 7.4 under conditions such that complexes are formed between the FcRn or a portion thereof and at least some of the candidate FcRn-binding antibodies;

(f) isolating the complexes formed in step (e);

(g) separating the candidate FcRn-binding antibodies from the isolated complexes of step (f);

(h) contacting the separated candidate FcRn-binding antibodies from step (g) with FcRn or a portion thereof at pH 6.0 under conditions such that complexes are formed between the FcRn or a portion thereof and at least some of the candidate FcRn-binding antibodies;

(i) isolating the complexes formed in step (h);

(j) separating the candidate FcRn-binding antibodies from the isolated complexes of step (i) to obtain antibodies that bind FcRn at both acidic pH and physiological pH.

(k) assaying the candidate FcRn-binding antibodies for ability to block albumin binding to FcRn.

In some embodiments, the collection of candidate FcRn-binding antibodies may be a library of antibodies or portions thereof (e.g., a library of scFvs displayed on phage).

In some embodiments, the concentration of FcRn or a portion thereof is decreased at each contacting step. For example, step (b) may be carried out at a concentration of 25 nM, step (e) may be carried out at a concentration of 2.5 nM, and step (h) may be carried out at a concentration of 0.25 nM.

In some embodiments, the FcRn or a portion thereof may be attached to a solid support, e.g., a magnetic bead. In such embodiments, the isolating steps may be simply the binding of the antibodies to the FcRn or a portion thereof attached to the solid support, e.g., when the solid support is a chromatography column. In some embodiments, the FcRn or a portion thereof may be attached to a moiety that facilitates isolation of the complexes between FcRn or a portion thereof and the antibodies. For example, the FcRn or a portion thereof may be attached to biotin.

Physical and functional properties of antibodies or antigen-binding portions thereof as set forth herein can be determined by routine procedures. For example, the ability of an antibody to block the FcRn-albumin interaction can be assessed by a number of methods. Such methods may include an in vitro assay examining the amount of albumin blocked from binding to FcRn by the antibody, a competitive assay against a known FcRn antibody that competes for binding with albumin, or an in vivo assay examining the amount of albumin secretion resulting from administration of the antibody.

Any of a variety of methods to detect disruption of binding between FcRn and albumin may be used, such as those described in U.S. Pat. No. 8,232,067, incorporated herein by reference in its entirety. For example, fluorescence resonance energy transfer ("FRET") or chromatographic methods may be used. In some cases, the protein-protein interaction may be detected by reconstituting domains of an enzyme, e.g., beta-galactosidase (see Rossi et al, Proc. Natl. Acad. Sci. USA, 94:8405-8410 (1997)). In some embodiments, testing of an antibody or antigen-binding fragment that disrupts the interaction between FcRn and albumin or for a variant albumin polypeptide that is deficient in binding FcRn can occur in an animal model. For example, methods of measuring the disruption between an FcRn polypeptide and an albumin polypeptide by an antibody or antigen-binding fragment include administering the antibody or antigen-binding fragment to a subject, e.g., an experimental animal (e.g., a mammal) expressing the FcRn polypeptide and the albumin polypeptide with an antibody or antigen-binding fragment and determining the level of the albumin polypeptide in a body fluid of the subject, wherein a difference in the level of albumin polypeptide in the body fluid of the subject in the presence of the antibody or antigen-binding fragment compared to the level of albumin polypeptide that would be present in the body fluid of the animal in the absence of the antibody or antigen-binding fragment indicates that the test compound disrupts the interaction between the FcRn polypeptide and the albumin polypeptide. In some embodiments, an animal to be used in accordance with one or more methods disclosed herein can be a transgenic animal. For example, an animal to be used in accordance with one or more methods disclosed herein can be transgenic such that it expresses FcRn, albumin, or both. In some embodiments, an animal can be transgenic such that it expresses a human FcRn, albumin, or both.

The specific region or epitope of human FcRn to which the antibodies disclosed herein bind can be identified by any suitable epitope mapping method known in the art. Such methods include screening peptides of varying lengths from FcRn for binding to the antibody in order to determine which amino acids of FcRn the antibody binds to. The peptides may be produced by well-known methods such as proteolytic digestion of FcRn or chemical synthesis. Techniques such as mass spectrometry may be used to identify peptides that bind the antibody. Alternatively, NMR spectroscopy or X-ray crystallography can be used. Once identified, the binding peptides may be used as immunogens to obtain additional antibodies which bind the same epitope of FcRn.

It is understood that the anti-FcRn antibodies or antigen-binding portions thereof set forth herein, where used in a mammal for the purpose of prophylaxis or treatment, will be administered in the form of a composition additionally comprising a pharmaceutically acceptable carrier. Suitable pharmaceutically acceptable carriers include, for example, one or more of water, saline, phosphate buffered saline, dextrose, histidine, glutamate, citrate, mannitol, trehalose, sucrose, arginine, acetate, Polysorbate 80, Poloxamer 188, and the like, as well as combinations thereof. Pharmaceutically acceptable carriers may further comprise minor amounts of auxiliary substances such as wetting or emulsifying agents, preservatives or buffers, which enhance the shelf life or effectiveness of the antibodies.

In some embodiments, the compositions comprising antibody and pharmaceutically acceptable carrier are lyophilized.

The compositions comprising antibody and pharmaceutically acceptable carrier may comprise the anti-FcRn antibodies or antigen-binding portions thereof set forth herein at various concentrations. For example, the compositions may comprise antibody at 10 mg/ml to 200 mg/ml, 25 mg/ml to 130 mg/ml, 50 mg/ml to 125 mg/ml, 75 mg/ml to 110 mg/ml, or 80 mg/ml to 100 mg/ml. The compositions also may comprise antibody at about 10 mg/ml, 20 mg/ml, 30 mg/ml, 40 mg/ml, 50 mg/ml, 60 mg/ml, 70 mg/ml, 80 mg/ml, 90 mg/ml, 100 mg/ml, 110 mg/ml, 120 mg/ml, 130 mg/ml, 140 mg/ml, or 150 mg/ml.

"albumin-bound toxin" refers to a compound, drug, or molecule that binds albumin. While it may be desirable under some circumstances to decrease the concentration of an albumin-bound toxin in a subject, the term is not limited to a compound, drug, or molecule that is labeled or commonly understood as a "toxin." The term may also include both exogenous or endogenous toxins. Albumin-bound toxins can include, for example, copper, hematin, long-chain fatty acid, zinc, bilirubin, thyroxine, eicosanoids, tryptophan, citamin D3, bile acids, calcium, magnesium, chloride, indomethacin, bromphenol blue, salicylate, warfarin, phenylbutazone, digoxin, furosemide, phenytoin, chlorpropamide, benzylpenicillin, Evans blue, diazepam, ibuprofen, naproxen, clofibrate, chlorpromazine, imipramine, quinidine, Ricin, amiodarone, and acetaminophen.

In one embodiment, provided is a method of reducing levels of albumin-bound toxins in a subject which comprises administering to the subject an amount of an antibody or antigen-binding fragment described herein effective to reduce levels of albumin-bound toxins. In some embodiments, the albumin-bound toxin may be exogenous or endogenous. In an embodiment, the albumin-bound toxin is copper, hematin, long-chain fatty acid, zinc, bilirubin, thyroxine, eicosanoids, tryptophan, vitamin D3, bile acids, calcium, magnesium, chloride, indomethacin, bromphenol blue, salicylate, warfarin, phenylbutazone, digoxin, furosemide, phenytoin, chlorpropamide, benzylpenicillin, Evans blue, diazepam, ibuprofen, naproxen, clofibrate, chlorpromazine, imipramine, quinidine, ricin, amiodarone, or acetaminophen. In some embodiments, the albumin-bound toxin may be acetaminophen. In other embodiments wherein the albumin-bound toxin may be acetaminophen, the method may further comprise the simultaneous, separate, or sequential administration of N-acetyl cysteine.

In another embodiment, provided is a method of preventing, treating, inhibiting, or reducing the severity of exposure to a toxin in a subject which comprise administering to the subject an effective amount of an antibody or antigen-binding fragment described herein. In some embodiments, the albumin-bound toxin may be exogenous or endogenous. In an embodiment, the toxin is copper, hematin, long-chain fatty acid, zinc, bilirubin, thyroxine, eicosanoids, tryptophan, vitamin D3, bile acids, calcium, magnesium, chloride, indomethacin, bromphenol blue, salicylate, warfarin, phenylbutazone, digoxin, furosemide, phenytoin, chlorpropamide, benzylpenicillin, Evans blue, diazepam, ibuprofen, naproxen, clofibrate, chlorpromazine, imipramine, quinidine, ricin, amiodarone, or acetaminophen. In some embodiments, the albumin-bound toxin may be acetaminophen. In other embodiments wherein the albumin-bound toxin may be acetaminophen, the method may further comprise the simultaneous, separate, or sequential administration of N-acetyl cysteine.

The methods described herein include methods for the treatment of disorders associated with albumin-bound toxins (e.g., with toxic levels of such toxins), e.g., from an overdose (e.g., from accidental or intentional exposure or ingestion to an amount of a toxin above a level considered safe for human or animal health) or from an endogenously high level of an albumin-binding toxin in a subject (e.g., from the subject producing a higher level of the toxin than what is considered normal and safe for human or animal health).

Provided here are methods of preventing or treating a medical condition associated with albumin toxicity which comprise administering to the subject an effective amount of an antibody or antigen-binding fragment described herein. As used herein, "albumin toxicity" refers to a state wherein albumin is considered deleterious or detrimental and may result in, e.g., death, organ damage, or neurological damage. In some embodiments, the medical condition is atherosclerotic coronary and peripheral vascular disease. In some embodiments, the medical condition is diabetic vasculopathic complications. In some embodiments, the medical condition is Alzheimer's disease. In some embodiments, the medical condition is traumatic brain injury. In some embodiments, the medical condition is diabetes mellitus. In some embodiments, the medical condition is end-stage kidney failure.

In the methods described herein, a therapeutically effective amount of an antibody or antigen-binding portions thereof set forth herein may be administered in combination (e.g. simultaneously, sequentially, or separately) with other agents, drugs, or hormones. In some embodiments, the other agents, drugs, or hormones may be known therapies for the respective medical condition. In some embodiments, the known therapies may be the standard of care. For example, in some embodiments of the methods reducing levels of albumin-bound toxins in a subject or methods of preventing, treating, inhibiting, or reducing the severity of exposure to a toxin in a subject, wherein the albumin-bound toxin is acetaminophen, the methods may further comprise the simultaneous, separate, or sequential administration of N-acetyl cysteine.

In some embodiments, blocking FcRn with an albumin-lowering agent would be beneficial in decreasing endogenous albumin levels to allow for enhanced pharmacokinetics and pharmacodynamics of an albumin-based therapeutic agent. In this instance, pre-treatment with an anti-FcRn antibody that is specific for the albumin binding site prior to administration of such a therapeutic agent will lower the competition derived from the endogenous albumin and allow for increased protection of the administered albumin-based therapeutic agent. In other embodiments, treatment with an anti-FcRn antibody that is specific for the albumin binding site may be used to clear albumin-based therapeutics from serum after administration. This may be useful where such albumin-based therapeutic treatment is no longer desired, or to reduce the side effects of a therapeutic overdose.

Albumin has been studied as a candidate for half-life extension and targeted intracellular delivery of drugs due to its interaction with FcRn. The term "albumin-based therapeutic agent" as used herein refers to therapeutic agents that are associated with albumin. An albumin-based therapeutic agent may be associated with albumin through, e.g., covalent conjugation, genetic fusion, or non-covalent association (see Larsen et al., Molecular and Cellular Therapies (2016) 4:3, incorporated herein by reference in its entirety). The association with albumin may occur prior to administration, i.e., the albumin-based therapeutic agent is associated with an exogenous albumin molecule or molecules. For example, albiglutide, manufactured by GlaxoSmithKline and marketed as Eperzan/Tanzeum for the treatment of type II diabetes, is a GLP-1 receptor agonist developed by fusion of two human GLP-1 repeats to recombinant human albumin. The association with albumin may occur after administration of the therapeutic agent, i.e., the albumin-based therapeutic agent is associated with an endogenous albumin molecule or molecules. For example, insulin detemir, manufactured by Novo Nordisk and marketed as Levemir for the treatment of type I diabetes, is a myristic acid modified insulin analog. On injection, the fatty acid moiety binds to albumin and dissociates over time, enhancing bioavailability and distribution. Other examples of albumin-based therapeutic agents include liraglutide, ozoralizumab, MTX-HSA, adloxorubicin, CJC-1134, Albuferon, Abraxane, ABI-008, ABI-009, ABI-010, $^{99M}$Tc-Albures, $^{99M}$Tc-Nanocoll, and others as described in Larsen et al.

In the methods described herein, a therapeutically effective amount of an antibody or antigen-binding portions thereof set forth herein is administered to a mammal in need thereof. The term "administering" as used herein means delivering the antibodies or antigen-binding portions thereof set forth herein to a mammal by any method that may achieve the result sought. They may be administered, for example, subcutaneously, intravenously or intramuscularly. Although antibodies or antigen-binding portions thereof set forth herein are particularly useful for administration to humans, they may be administered to other mammals as well. The term "mammal" as used herein is intended to include, but is not limited to, humans, laboratory animals, domestic pets and farm animals. "Therapeutically effective amount" means an amount of antibody or antigen-binding portions thereof set forth herein that, when administered to a mammal, is effective in producing the desired therapeutic effect. For example, depending on the disease, for an antibody, this may require 0.1, 1.0, 3.0, 6.0, or 10.0 mg/Kg. For an IgG having a molecular mass of 150,000 g/mole (two binding sites), these doses correspond to approximately 18 nM, 180 nM, 540 nM, 1.08 µM, and 1.8 µM of binding sites for a 5 L blood volume.

In certain embodiments, the antibody or antigen-binding portion thereof is administered to the mammal by intravenous infusion, i.e., introduction of the antibody or antigen-binding portion thereof into the vein of a mammal over a certain period of time. In certain embodiments, the period of time is about 5 minutes, about 10 minutes, about 30 minutes, about 1 hour, about 2 hours, about 4 hours, or about 8 hours.

In certain embodiments, the antibody or antigen-binding portion thereof is administered to the mammal by subcutaneous delivery, i.e., under the skin of the mammal, generally by pinching and lifting the skin away from underlying tissue and injecting the antibody or antigen-binding portion thereof into the space under the skin thereby formed.

In certain embodiments, a dose of a compound or a composition is administered to a subject every day, every other day, every couple of days, every third day, once a week, twice a week, three times a week, or once every two weeks. In other embodiments, two, three or four doses of a compound or a composition is administered to a subject every day, every couple of days, every third day, once a week or once every two weeks. In some embodiments, a dose(s) of a compound or a composition is administered for 2 days, 3 days, 5 days, 7 days, 14 days, or 21 days. In certain embodiments, a dose of a compound or a composition is administered for 1 month, 1.5 months, 2 months, 2.5 months, 3 months, 4 months, 5 months, 6 months or more. in some embodiments, the compound or composition may be administered prior to, contemporaneously with, or subsequently to exposure to a toxin.

Methods of administration include but are not limited to parenteral, intradermal, intravitrial, intramuscular, intraperitoneal, intravenous, subcutaneous, intranasal, epidural, oral, sublingual, intranasal, intracerebral, intravaginal, transdermal, transmucosal, rectally, by inhalation, or topically, particularly to the ears, nose, eyes, or skin. The mode of administration is left to the discretion of the practitioner. In most instances, administration will result in the release of a compound into the bloodstream.

In specific embodiments, it may be desirable to administer a compound locally. This may be achieved, for example, and not by way of limitation, by local infusion, topical application, by injection, by means of a catheter, or by means of an implant, said implant being of a porous, non-porous, or gelatinous material, including membranes, such as sialastic membranes, or fibers. In such instances, administration may selectively target a local tissue without substantial release of a compound into the bloodstream.

Pulmonary administration can also be employed, e.g., by use of an inhaler or nebulizer, and formulation with an aerosolizing agent, or via perfusion in a fluorocarbon or synthetic pulmonary surfactant. In certain embodiments, a compound is formulated as a suppository, with traditional binders and vehicles such as triglycerides.

In another embodiment, a compound is delivered in a vesicle, in particular a liposome (See Langer, 1990, Science 249:1527-1533; Treat et al., in Liposomes in the Therapy of Infectious Disease and Bacterial infection, Lopez-Berestein and Fidler (eds.), Liss, New York, pp. 353-365 (1989); Lopez Berestein, ibid., pp. 317-327; see generally ibid.).

In another embodiment, a compound is delivered in a controlled release system (See, e.g., Goodson, in Medical Applications of Controlled Release, supra, vol. 2, pp. 115-138 (1984)). Examples of controlled-release systems are discussed in the review by Langer, 1990, Science 249:1527-1533 may be used. In one embodiment, a pump may be used (See Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (See Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23:61; See also Levy et al., 1985, Science 228:190; During et al., 1989, Ann. Neurol. 25:351; Howard et al., 1989, J. Neurosurg. 71:105).

Toxicity and therapeutic efficacy can be measured by standard pharmaceutical procedures in cell cultures or experimental animals to determine, for example, the LD50 (the dose lethal to 50% of the population) and the ED50 (the dose therapeutically effective in 50% of the population). The dose ratio, expressed as the ration between LD50/ED50, is known as the therapeutic index. Antibodies or antigen-binding fragments which exhibit high therapeutic indices are preferred.

The formulation of a dosage range for use in humans may be obtained from data from cell culture assays and/or animal studies, and preferably lies within the range of circulating concentrations that includes the ED50 with little or no toxicity. The dosage may vary within this range depending upon the dosage form employed and the route of administration utilized. The skilled artisan will appreciate that certain factors influence the dosage and timing required to effectively treat a patient, including but not limited to the type of patient to be treated, the severity of the disease or disorder, previous treatments, the general health and/or age of the patient, and other disorders present. Moreover, treatment of a patient with a therapeutically effective amount of an antibody or antigen-binding fragment can include a single treatment, or can include a series of treatments.

The above-described administration schedules are provided for illustrative purposes only and should not be considered limiting. A person of ordinary skill in the art will readily understand that all doses are within the scope of the invention.

It is to be understood and expected that variations in the principles of invention herein disclosed may be made by one skilled in the art and it is intended that such modifications are to be included within the scope of the present invention.

Throughout this application, various publications are referenced. These publications are hereby incorporated into this application by reference in their entireties to more fully describe the state of the art to which this invention pertains. The following examples further illustrate the invention, but should not be construed to limit the scope of the invention in any way.

EXAMPLES

Example 1

Humanization of Variable Domains

Heavy and light chain variable regions suitable for human administration were designed based on a mouse monoclonal antibody selected for its ability to bind to FcRn and block the binding of FcRn and albumin. The mouse antibody does not substantially block the binding of FcRn and IgG Fc. Using a model of the monoclonal antibody based on existing antibody structures, variable region frameworks for the human antibody were designed from segments of human V regions. In order to minimize potential immunogenicity, several variants were designed with amino acids selected at certain framework locations designed to remove human T cell epitopes.

Heavy and light chain V region genes were constructed from overlapping oligonucleotides assembled into full length genes using the ligase chain reaction (LCR), followed by amplification and addition of restriction sites suitable for cloning.

Three heavy chains variants were constructed with a human IgG4 constant region containing the S241P mutation. The variants are designated $V_H1$, $V_H3$, and $V_H4$. The amino acid sequences of the variable domains of the heavy chain variants are represented by SEQ ID NOS:12, 14, and 16, respectively. The oligonucleotide sequences of the variable domains of the heavy chain variants are represented by SEQ ID NOS:11, 13, and 15, respectively. FIG. 1 shows an alignment of the three variants. Four light chain variants were constructed and expressed as human kappa chains. The variants are designated Vκ1, vκ2, vκ3, and Vκ4. The amino acid sequences of the light chain variants are represented by SEQ ID NOS:18, 20, 22, and 24, respectively. The oligonucleotide sequences of the variable domains of the light chain variants are represented by SEQ ID NOS:17, 19, 21, and 23, respectively. FIG. 2 shows an alignment of the four variants.

Antibodies were expressed as whole IgGs by cloning V region genes into a mammalian expression vector with an upstream cytomegalovirus immediate/early promoter/enhancer, an immunoglobulin signal sequence, and immunoglobulin constant region. The vectors were transfected into HEK EBNA cells, expression quantified, and antibodies purified on Protein A columns.

All 12 heavy-light chain combinations of the three heavy chain and four light chain variants were expressed by transient transfection into HEK EBNA cells. The antibodies were purified on Protein A sepharose columns and quantified. As indicated above, FcRn resides primarily in the early acidic endosomes where it captures endocytosed albumin at a low pH. To block binding of FcRn to albumin, it is also desirable that the FcRn antibodies will bind to FcRn exposed to the intercellular milieu at physiologic pH (e.g., pH 7.4). Therefore, the binding of the purified antibodies to FcRn was assessed in a competition ELISA assay at pH 6.0 and pH 7.4.

For the ELISA, a Nunc Immuno MaxiSorp 96 well flat bottom microtitre plate was pre-coated overnight at pH 7.4 with an FcRn antibody specific for an IgG-binding epitope distinct from the albumin-binding region. The following day 1 µg/ml recombinant human FcRn (Sino Biological Inc. Cat. No. CT009-H08H) diluted in PBS pH 7.4 was added to the wells and incubated for 1 hour at 37° C. A four-fold dilution series of test or control IgG4 antibodies from 30 µg/ml to 0.0018 µg/ml was premixed with a constant concentration of biotinylated parent murine antibody, added to the plates and incubated for 1 hour at 37° C. The binding of the biotinylated mAb was detected with streptavidin-HRP and TMB substrate. Absorbance was read at 450 nm and the binding curves plotted. The binding of the 12 combinations was tested at both pH 7.4 and pH 6.0 and quantified by comparison to the parent antibody, as shown in Table 2.

TABLE 2

| | | Relative Affinity | |
|---|---|---|---|
| | | Average relative IC$_{50}$ (relative to chimeric parent IgG$_4$) | |
| Variant | Average titer (µg/ml) | pH 7.4 | pH 6 |
| chimeric parent | 10.30 | 1 | 1 |
| V$_H$1/Vκ1 | 27.92 | 0.51 | 0.64 |
| V$_H$1/Vκ2 | 25.61 | 0.29 | 0.45 |
| V$_H$1/Vκ3 | 27.93 | 0.37 | 0.56 |
| V$_H$1/Vκ4 | 28.00 | 0.45 | 0.75 |
| V$_H$3/Vκ1 | 33.05 | 1.39 | 1.09 |
| V$_H$3/Vκ2 | 24.27 | 1.24 | 0.90 |
| V$_H$3/Vκ3 | 24.76 | 0.50 | 0.52 |
| V$_H$3/Vκ4 | 21.56 | 0.58 | 0.61 |
| V$_H$4/Vκ1 | 37.18 | 1.06 | 1.06 |
| V$_H$4/Vκ2 | 38.71 | 1.06 | 1.06 |
| V$_H$4/Vκ3 | 33.95 | 1.24 | 0.86 |
| V$_H$4/Vκ4 | 34.95 | 1.37 | 0.99 |

Example 2

Affinity Maturation

To improve binding affinity at acidic and physiologic pH, the heavy and light chain variable domain CDR3 regions were mutated and screened in scFv form at pH 6.0 and pH 7.4. To prepare scFvs, genes encoding $V_H$ and Vκ were assembled with a 15 amino acid (G$_4$S)$_3$ linker using overlap PCR. The scFv sequence was cloned into a phagemid vector as a gene 3 fusion protein, and the vector transformed into *E. coli* (TG1). The affinity maturation process was conducted using the $V_H1$ and $V_κ1$ variants. For screening, a library of heavy chain CDR3s in $V_H1$ was combined with the humanized parental Vκ1 light chain and a library of light chain CDR3s in $V_H1$ was combined with the humanized parental $V_H1$ heavy chain.

Amino acid sequence variation was introduced into the heavy chain CDR3H region at amino acid positions 94-100 (a.a. 95-100 of CDR3H and a.a. 94 of FW3) using an oligonucleotide comprising the sequence ARGBNSVVSBNCVNCNVCRSC (SEQ ID NO:41) which provided for selected amino acids at each position as follows: a.a. 94: K, R; a.a. 95: A, C, D, E, F, G, H, I, L, P, Q, R, S, V, W, Y; a.a. 96: A, D, E, G, H, K, N, P, Q, R, S, T; a.a. 97: A, C, D, F, G, H, L, P, R, S, T, V, Y; a.a. 98: A, D, G, H, I, L, N, P, R, S, T, V; a.a. 99: A, C, D, G, H, N, P, R, S, T, Y; a.a. 100: A, G, S, T. Amino acid sequence variation was introduced into the heavy chain CDR3H region at amino acid positions 94-99 (a.a. 95-99 of CDR3H and a.a. 94 of FW3) using an oligonucleotide comprising the sequence AGGNNSNNSNNSNNSRSC (SEQ ID NO:42) which provided for selected amino acids at each position as follows: a.a. 94: R; a.a. 95: A, C, D, E, F, G, H, I, K, L, M, N, P, Q, R, S, T, V, W, Y; a.a. 96: A, C, D, E, F, G, H, I, K, L, M, N, P, Q, R, S, T, V, W, Y; a.a. 97: A, C, D, E, F, G, H, I, K, L, M, N, P, Q, R, S, T, V, W, Y; a.a. 98: A, C, D, E, F, G, H, I, K, L, M, N, P, Q, R, S, T, V, W, Y; a.a. 99: A, G, S, T.

For each CDR, a library of about 5-10×10⁷ phage containing on the order of 3-6×10⁶ DNA sequences (i.e., about 10-20 copies of each DNA sequence were represented) was screened for binding to soluble antigen. Specifically, the phage libraries were mixed with soluble biotinylated FcRn, followed by capture of FcRn-antibody phage complexes on streptavidin-coated beads. To obtain antibodies that bind to FcRn in acidic endosomes as well as at physiologic pH, successive rounds of library screening were conducted at alternating pH. Also, to increase the stringency of each successive screening round, the concentration of FcRn antigen was reduced. The initial selection round was conducted with an FcRn concentration of 25 nM at pH 6.0. The second round was conducted at 2.5 nM at pH 7.4. The third round was conducted at 0.25 nM at pH 6.0. During the third round, an "Off-Rate" selection was conducted at 0.25 nM at pH 6.0. The fourth round was conducted at 0.1 nM at pH 7.4.

The scFv antibodies were prepared from bacterial periplasmic extracts, and tested by competition ELISA at pH 6.0 and pH 7.4. Of greater than 4100 peripreps analysed at pH 6.0, 99 were selected for further analysis at pH 7.4. In the competition ELISA, the scFv antibody fragments were competed against biotinylated parent murine antibody, which was previously shown to block the FcRn-albumin interaction, for binding to immobilized FcRn. As in the ELISA used to test humanized variants, a 96 well flat bottom microtitre plate was pre-coated with 1 µg/ml of an FcRn antibody specific for an IgG-binding epitope distinct from the albumin-binding region. Binding was determined at pH 7.4 and pH 6.0. FIG. 3 shows a comparison of competition ELISA at pH 6.0 and pH 7.4 in relation to the parent scFv (i.e., consisting of $V_H1/V_\kappa1$).

Substantial improvements in binding were measured for scFvs containing affinity matured heavy chain CDR3s in the $V_H1$ framework. Therefore these heavy chains were carried forward for testing in combination with improved light chains Improved variants were not identified for scFvs containing affinity matured light chain CDR3s in the Vκ3 framework.

Example 3

Development of IgG Antibodies

Twenty one affinity matured heavy chains (G03_B2, G15_C10, G15_C3, G15_B7, G02_F4, G24_C11, G19_F8, G47_B10, G47_H11, G48_G10, G48_E3, G49_F11, G50_B10, G50_G5, G50_C10, G54_D11, G52_G9, G51_H6, G49_H9.3, or G49_H9.5) were selected and expressed with a humanized light chain (Vκ3). The twenty one combinations were expressed as bivalent IgG4 antibodies containing the S241P mutation by transient transfection of HEK cells, followed by purification of the IgG4 antibodies.

Example 4

Antigen Binding Characteristics of IgG4 Antibodies as Determined by ELISA

Figure 4A:
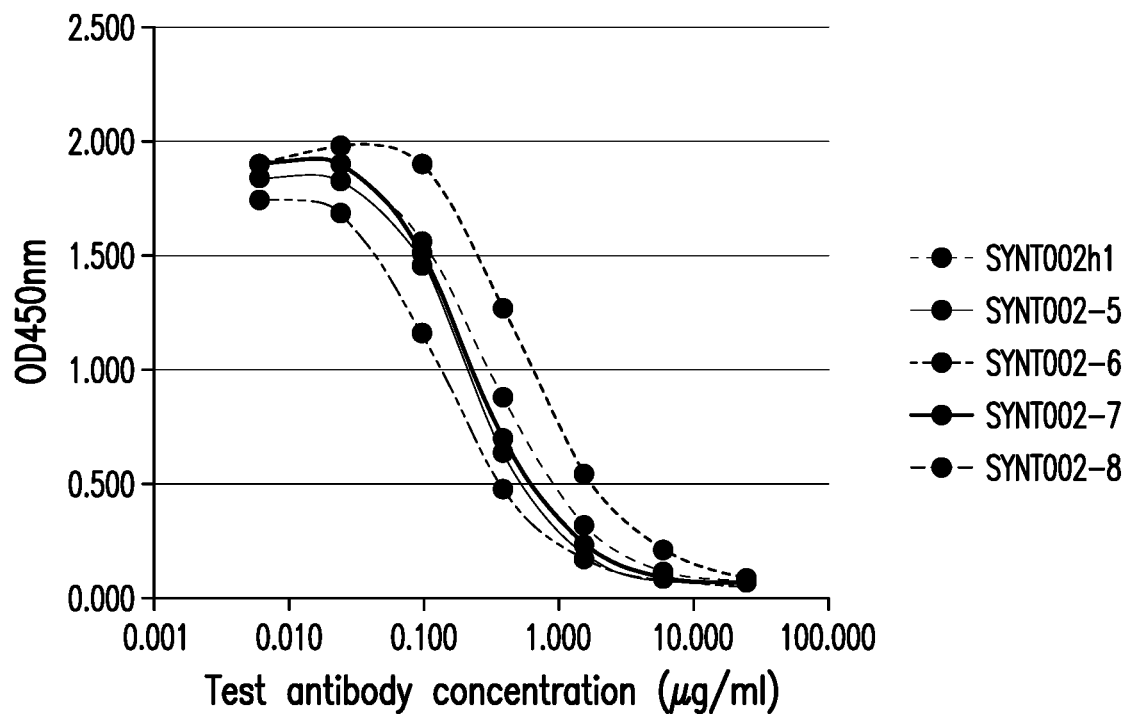
FIG. 4 shows anti-FcRn competition ELISA testing of humanized affinity matured anti-FcRn antibodies at either (a) pH 7.4 or (b) pH 6.0. IgGs were transiently expressed in HEK cells. A dilution series of anti-FcRn humanized affinity matured variants was tested against a fixed concentration of biotinylated murine parent for binding to recombinant human FcRn at either pH 7.4 or pH 6.0. Bound biotinylated murine parent was detected using streptavidin-HRP and TMB substrate.
Figure 4B:
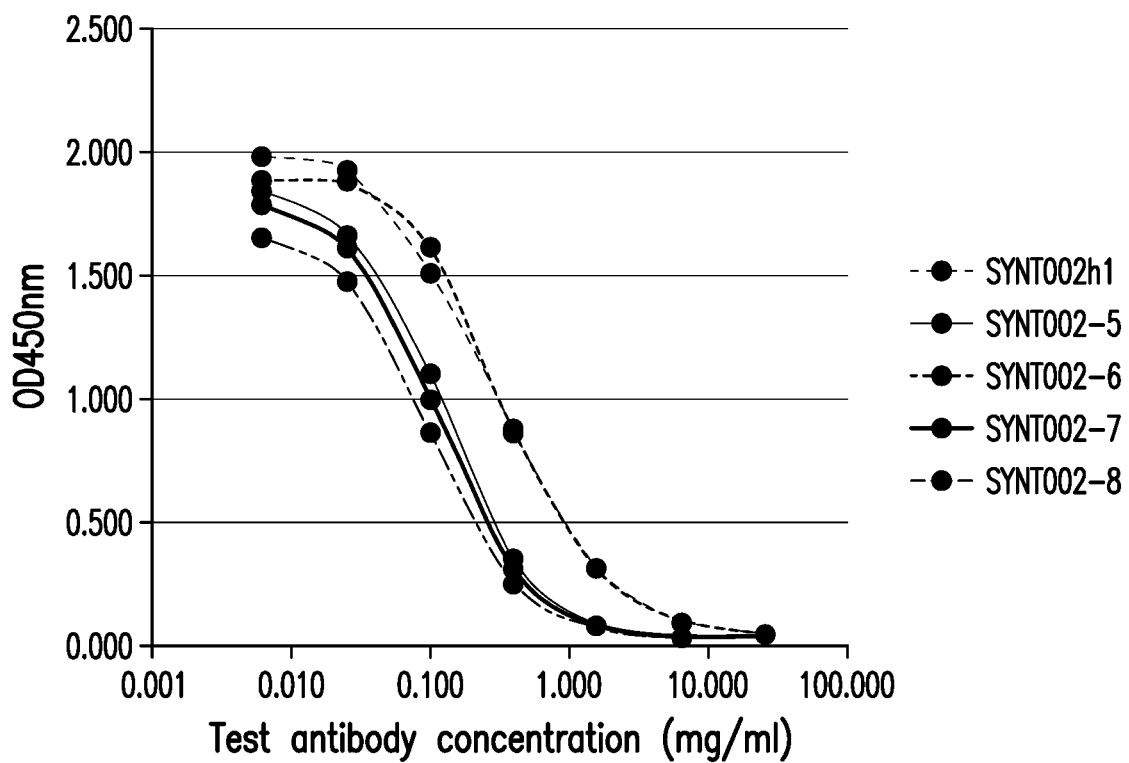

The IgG4 antibodies were tested for antigen binding in a competition ELISA at pH 6.0 and pH 7.4. A Nunc Immuno MaxiSorp 96 well flat bottom microtitre plate (Fisher, cat. no. DIS-971-030J) was pre-coated with 1 µg/ml of an FcRn antibody specific for an IgG-binding epitope distinct from the albumin-binding region overnight at pH 7.4. The following day, 1 µg/ml recombinant human FcRn (Sino Biological Inc. cat. no. CT009-H08H) diluted in PBS pH 7.4 was added to the wells and incubated for 1 hour at 37° C. After washing the plates 3× with PBST pH 7.4, the plates were blocked with PBSM pH 7.4 for 1 hour at 37° C. From this point onwards, all wash and incubation steps were performed at the chosen assay pH (pH 6.0 or 7.4). After washing 3× with PBST, a four-fold dilution series of tested antibodies from 25 µg/ml to 0.006 µg/ml final concentration was premixed with a constant concentration of biotinylated parent murine antibody (0.4 µg/ml, final concentration), added to the FcRn coated plates and incubated for 1 hour at 37° C. Following 3×PBST washes, the binding of the biotinylated mAb was detected with streptavidin-HRP (Sigma, cat. no. 55512) and TMB substrate (Invitrogen, cat. no. 00-2023). The reaction was stopped with 3 M HCl, absorbance read at 450 nm on a Dynex Technologies MRX TC II plate reader and the binding curves plotted. An example of data for four of the antibodies (G02_F4$V_H$1_Vκ3, G24_C11$V_H$1_Vκ3, G19_F8$V_H$1_Vκ3, G47_B10$V_H$1_Vκ3) is shown at pH 7.4 in FIG. 4(a) and at pH 6.0 in FIG. 4(b). The full results obtained are summarized in Table 3, which shows the average relative $IC_{50}$ values for experiments performed at pH 7.4 and pH 6.0 and the number (n) of experiments. $IC_{50}$ values of the combinations were normalized to the humanized parent antibody tested on the same plate.

TABLE 3

Relative Affinity

| Variant | Average relative $IC_{50}$ (relative to humanized parent) | |
|---|---|---|
| | pH 7.4 | pH 6 |
| $V_H$1/Vκ1 | 1 | 1 |
| G03_B2/Vκ3 | 4.3 | 9.1 |
| G15_C10/Vκ3 | 0.6 | 0.7 |
| G15_C3/Vκ3 | 0.8 | 0.9 |
| G15_B7/Vκ3 | 2.0 | 8.2 |
| G02_F4/Vκ3 | 0.8 | 0.6 |
| G24_C11/Vκ3 | 2.6 | 1.5 |
| G19_F8/Vκ3 | 0.9 | 0.7 |
| G47_B10/Vκ3 | 0.6 | 0.6 |
| G47_H11/Vκ3 | 1.5 | 1.0 |
| G47_H6/Vκ3 | 0.7 | 0.8 |
| G48_G10/Vκ3 | 2.4 | 1.0 |
| G48_E3/Vκ3 | 3.6 | 2.3 |
| G49_F11/Vκ3 | 1.5 | 1.0 |
| G50_B10/Vκ3 | 1.1 | 1.0 |
| G50_G5/Vκ3 | 1.2 | 0.9 |
| G50_C10/Vκ3 | 0.7 | 0.9 |
| G54_D11/Vκ3 | 0.8 | 0.6 |
| G52_G9/Vκ3 | 0.8 | 0.8 |
| G51_H6/Vκ3 | 2.9 | 2.3 |
| G49_H9.3/Vκ3 | 0.7 | 0.8 |
| G49_H9.5/Vκ3 | 1.0 | 0.8 |

Fourteen combinations with equal or better activity than the humanized parent at either pH 6.0 or pH 7.4 were identified and taken forward for stable transfection into NS0 mouse myeloma cells.

Example 5

Stable Expression and Purification of Antibodies pAnt vector DNA encoding the 14 IgG combinations (G15_C10/$V_\kappa$3, G15_C3/$V_\kappa$3, G02_F4/$V_\kappa$3, G19_F8/$V_\kappa$3, G47_B10/$V_\kappa$3, G47_H6/$V_\kappa$3, G49_F11/$V_\kappa$3, G50_B10/$V_\kappa$3, G50_G5/$V_\kappa$3, G50_C10/$V_\kappa$3, G54_D11/$V_\kappa$3, G52_G9/$V_\kappa$3, G49_H9.3/$V_\kappa$3, or G49_H9.5/$V_\kappa$3) with equal or better activity than the humanized parent (i.e., consisting of $V_H1/V_\kappa1$) were stably transfected into NS0 mouse myeloma cells via electroporation. In addition, the preferred humanized antibody, $V_H1/V_\kappa3$, was included. Stable transfections were initially selected using 200 nM methotrexate which was increased to 500 nM during expansion. Methotrexate-resistant colonies for each construct were tested for IgG expression levels using an IgG4 ELISA, and the best expressing lines were selected, expanded and frozen under liquid nitrogen. Successful transfection and stable clone selection was achieved for all 14 humanized variants as well as $V_H1/V_\kappa3$.

Antibodies were purified from cell culture supernatants on Protein A sepharose columns, buffer exchanged into PBS pH 7.2 and quantified by $OD_{280nm}$ using an extinction coefficient based on the predicted amino acid sequence.

Figure 5:
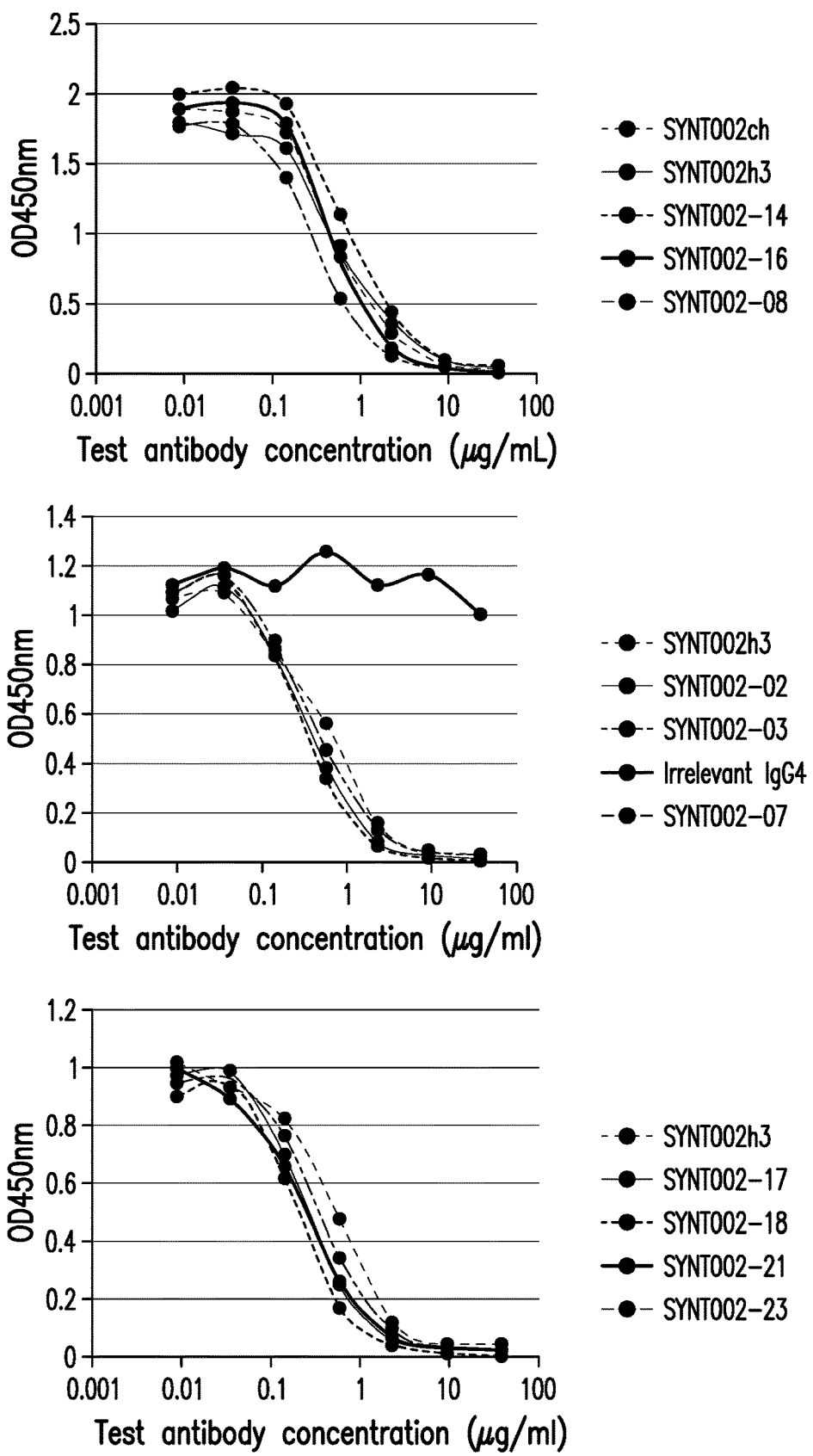
FIG. 5 shows anti-FcRn competition ELISA testing of humanized affinity matured anti-FcRn antibodies at pH 6.0. IgGs were stably expressed in NS0 cells. A dilution series of anti-FcRn humanized affinity matured variants was tested against a fixed concentration of biotinylated murine parent for binding to recombinant human FcRn at pH 6.0. Bound biotinylated murine parent was detected using streptavidin-HRP and TMB substrate.
Figure 6:
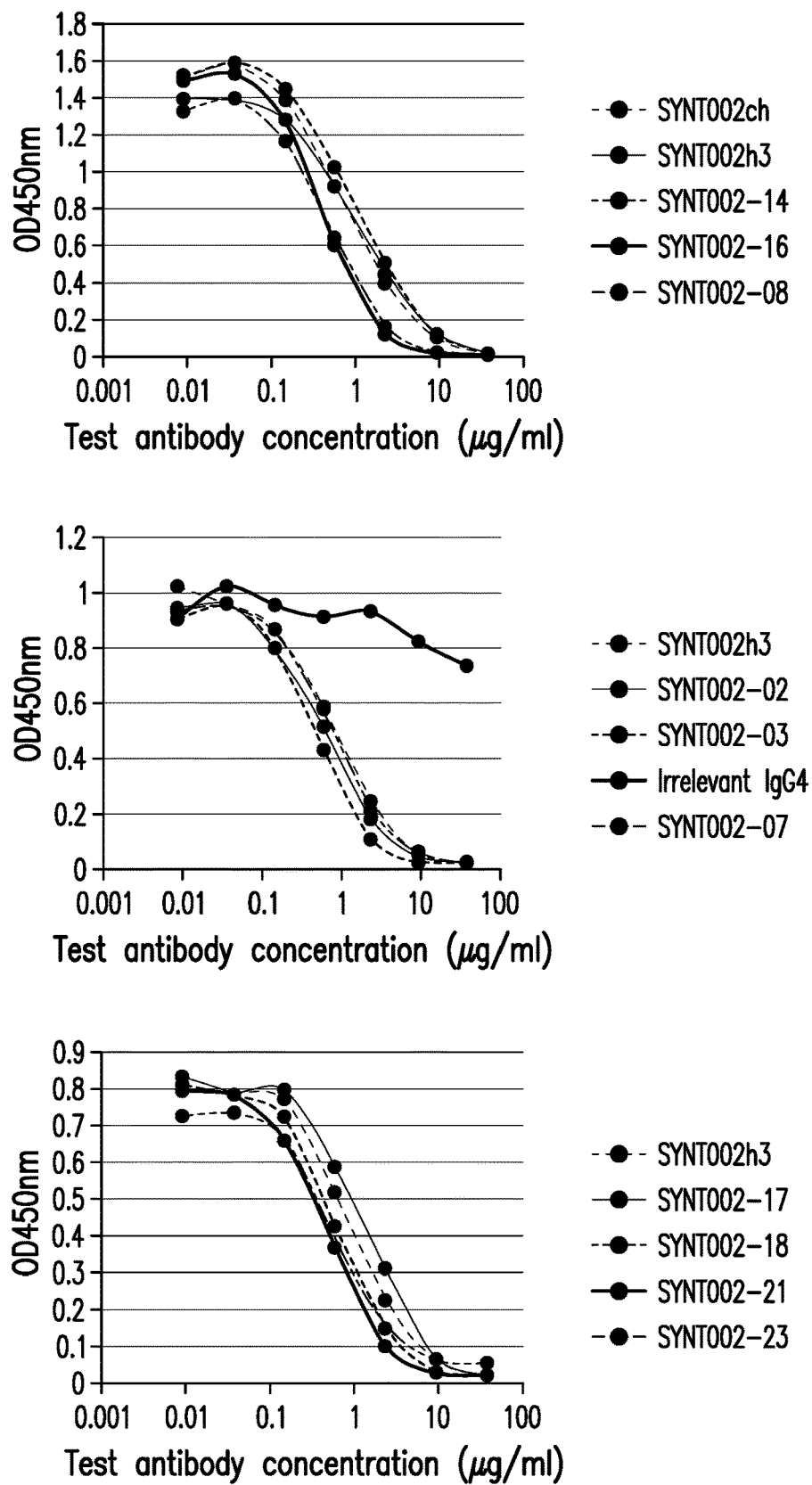
FIG. 6 shows anti-FcRn competition ELISA testing of humanized affinity matured anti-FcRn antibodies at pH 7.4. IgGs were stably expressed in NS0 cells. A dilution series of anti-FcRn humanized affinity matured variants was tested against a fixed concentration of biotinylated murine parent for binding to recombinant human FcRn at pH 7.4. Bound biotinylated murine parent was detected using streptavidin-HRP and TMB substrate.
Figure 7A:
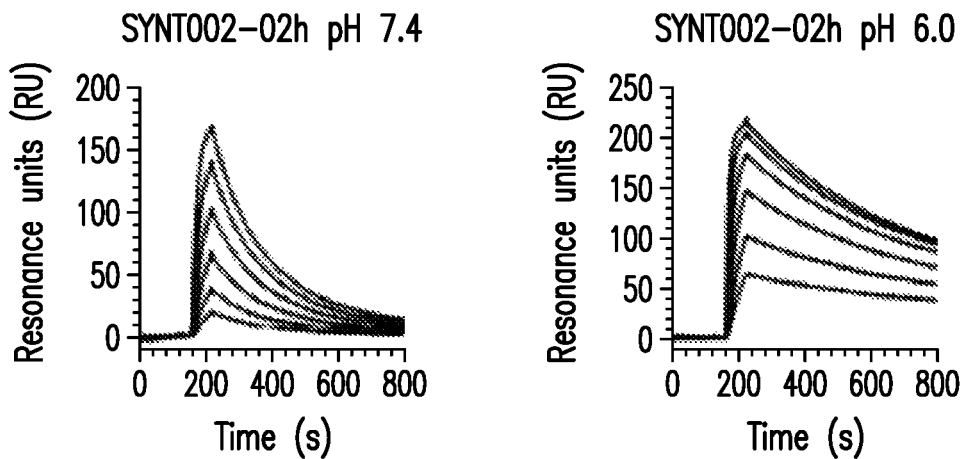
FIG. 7 shows the binding of mAbs to human FcRn at pH 7.4 and pH 6.0. Representative sensorgrams showing binding of titrated amounts of hFcRn injected over the immobilized mAbs (A) SYNT002h (humanized parent $V_H1/V\kappa1$), (B) SYNT002-3 (G15_C3/$V_\kappa3$), (C) SYNT002-8 (G47_B10/$V_\kappa3$), (D) SYNT002-16 (G50_C10/$V_\kappa3$), (E) SYNT002-17 (G54_D11/$V_\kappa3$), and (F) SYNT002-21 (G49_H9.3/$V_\kappa3$).
Figure 7B:
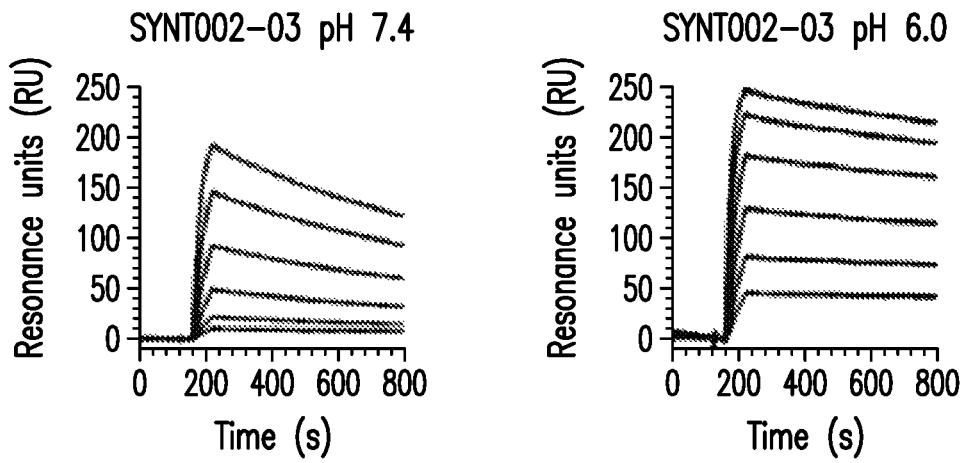
Figure 7C:
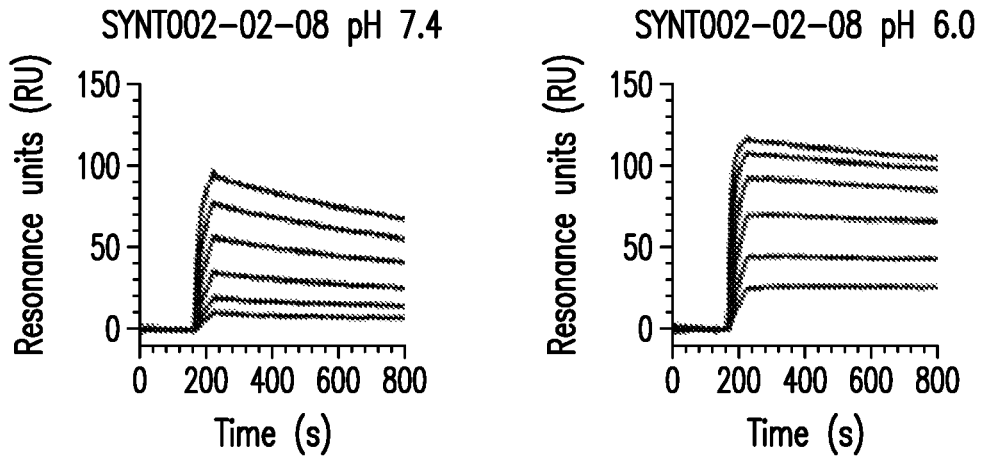
Figure 7D:
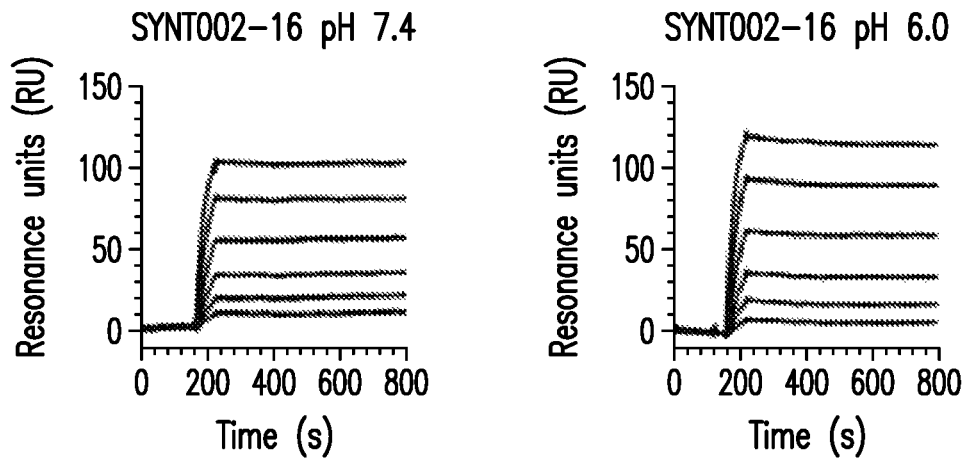
Figure 7E:
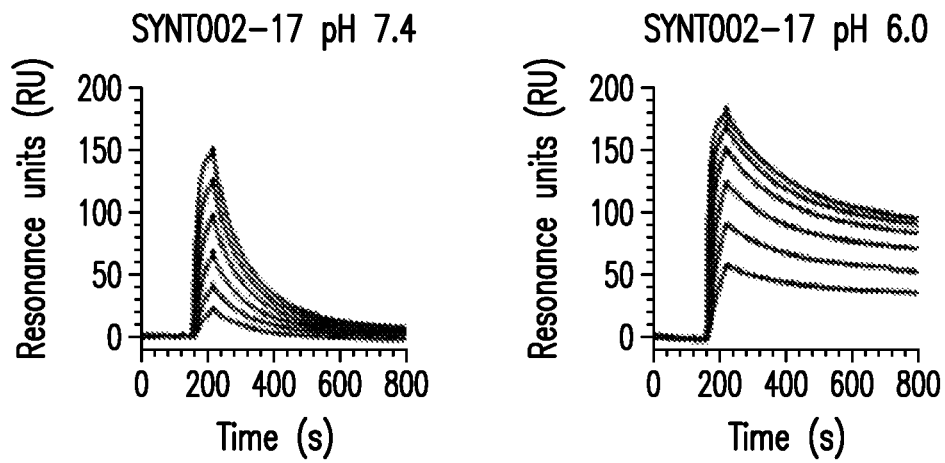
Figure 7F:
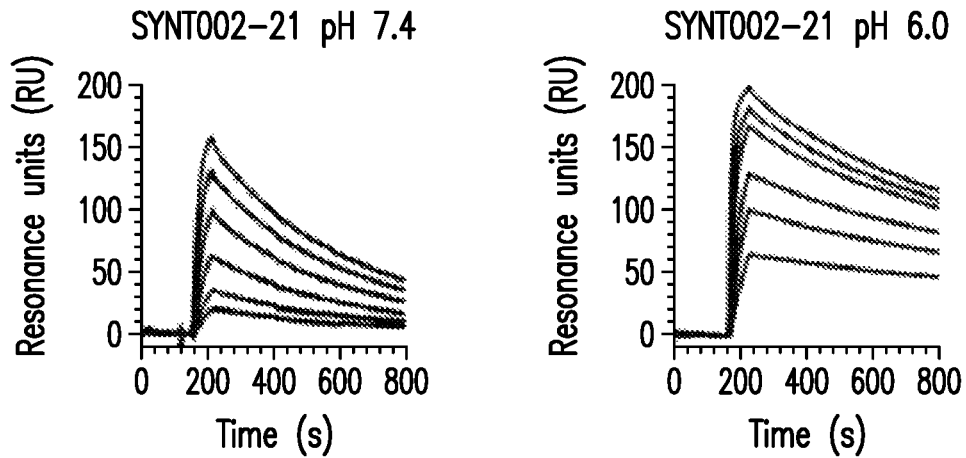

The binding of humanized affinity matured antibodies to FcRn was tested at both pH 7.4 and pH 6.0 by competition ELISA as described above and compared to the chimeric parent. NS0 produced humanized affinity matured IgGs were used in all assays other than G50_C10/$V_\kappa3$, which was purified from transiently expressing HEK cells. Example data at pH 6.0 is shown in FIG. 5, and example data at pH 7.4 is shown in FIG. 6. The data is summarized in Table 4 below.

TABLE 4

Relative Affinity

| Variant | Average relative $IC_{50}$ (relative to humanized parent) | |
|---|---|---|
| | pH 7.4 | pH 6 |
| $V_H1/V\kappa3$ | 1 | 1 |
| G15_C10/V$\kappa$3 | 0.98 | 0.78 |
| G15_C3/V$\kappa$3 | 0.80 | 0.68 |
| G02_F4/V$\kappa$3 | 1.10 | 0.95 |
| G19_F8/V$\kappa$3 | 1.19 | 0.76 |
| G47_B10/V$\kappa$3 | 0.74 | 0.58 |
| G47_H6/V$\kappa$3 | 0.89 | 0.84 |
| G49_F11/V$\kappa$3 | 1.35 | 0.98 |
| G50_B10/V$\kappa$3 | 1.29 | 1.23 |
| G50_G5/V$\kappa$3 | 1.63 | 0.84 |
| G50_C10/V$\kappa$3 | 0.54 | 0.89 |
| G54_D11/V$\kappa$3 | 1.93 | 0.62 |
| G52_G9/V$\kappa$3 | 0.92 | 0.56 |
| G49_H9.3/V$\kappa$3 | 0.73 | 0.58 |
| G49_H9.5/V$\kappa$3 | 0.87 | 0.80 |

Eight of the variants (G15_C3/$V_\kappa3$, G47_B10/$V_\kappa3$, G47_H6/$V_\kappa3$, G50_C10/$V_\kappa3$, G54_D11/$V_\kappa3$, G52_G9/$V_\kappa3$, G49_H9.3/$V_\kappa3$, and G49_H9.5/$V_\kappa3$) were improved at both pH 6.0 and pH 7.4 compared to the preferred humanized variant. One antibody was improved at pH 6.0 but not at pH 7.4. These eight antibodies were taken forward for Biacore analysis.

Example 6

Determination of mAb Binding Kinetics Using Surface Plasmon Resonance

Binding kinetics of the selected variants were compared to the murine parent and humanized parent ($V_H1/V\kappa1$) by BIACORE® using a T200 Instrument. Antibodies were immobilized onto a Series S CM5 sensor chip surface using standard amine coupling chemistry and analyte (FcRn) flowed over the surface. A 2-fold dilution range was selected from 50-0.01 nM FcRn. The association phase of FcRn analyte was monitored for 450 seconds, and dissociation was initially measured for either 250 or 2500 seconds, at 40 µl/min $F_c1$ was a reference channel and was subtracted from other flow cells to correct for non-specific binding. The fold difference in $K_D$ was calculated by dividing the $K_D$ of the humanized parent by that of the test antibody on the same chip. Kinetic values are based on a 1:1 binding model (Table 5).

The affinity matured humanized antibodies G15_C3/$V_\kappa3$, G47_B10/$V_\kappa3$, and G50_C10/$V_\kappa3$ showed significant improvements in affinity when compared to the humanized parental (ranging from between ~7.1 to ~50 fold on average). The slow off rate observed for G50_C10/$V_\kappa3$ was approaching the limits of detection of the Biacore instrument. The three best variants were assayed again to provide a direct ranking comparison with the dissociation time increased to 4500 seconds in order to more accurately determine the dissociation constant for G50_C10/$V_\kappa3$.

TABLE 5

Binding kinetics of anti-human FcRn mAbs

| mAbs | $F_c$ | $K_a$ (1/Ms) | $K_d$ (1/s) | $K_D$ (nM) | $\chi^2$ | Fold difference in $K_D$ |
|---|---|---|---|---|---|---|
| Murine Parent | 2 | 4.75E+05 | 1.29E−03 | 2.7 | 0.02 | 0.9 |
| $V_H1/V\kappa1$ | 3 | 4.77E+05 | 1.16E−03 | 2.43 | 0.08 | 1.0 |
| G47_B10/$V_\kappa3$ | 4 | 4.15E+05 | 1.34E−04 | 0.33 | 0.07 | 7.4 |
| $V_H1/V\kappa1$ | 2 | 5.37E+05 | 1.10E−03 | 2.05 | 0.02 | 1.0 |
| G15_C3/$V_\kappa3$ | 3 | 6.68E+05 | 1.96E−04 | 0.29 | 0.06 | 7.1 |
| G50_C10/$V_\kappa3$ (HEK) | 4 | 3.99E+05 | 1.00E−05 | 0.025 | 0.07 | 82 |
| $V_H1/V\kappa1$ | 2 | 5.17E+05 | 1.02E−03 | 1.97 | 0.08 | 1.0 |
| G52_G9/$V_\kappa3$ | 3 | 4.55E+05 | 9.04E−04 | 1.99 | 0.06 | 1.0 |
| G49_H9.3/$V_\kappa3$ | 4 | 5.47E+05 | 6.08E−04 | 1.11 | 0.09 | 1.8 |
| $V_H1/V\kappa1$ | 2 | 4.47E+05 | 1.17E−03 | 2.61 | 0.08 | 1.0 |
| G47_H6/$V_\kappa3$ | 3 | 3.89E+05 | 8.14E−04 | 2.09 | 0.05 | 1.2 |
| G49_H9.5/$V_\kappa3$ | 4 | 1.5E+05 | 1.81E−04 | 1.21 | 0.07 | 2.2 |
| $V_H1/V\kappa1$ | 2 | 4.72E+05 | 1.10E−03 | 2.34 | 0.04 | 1.0 |
| G54_D11/$V_\kappa3$ | 3 | 5.67E+05 | 2.10E−03 | 3.71 | 0.03 | 0.6 |
| G50_C10/$V_\kappa3$ | 4 | 2.98E+05 | 2.34E−05 | 0.078 | 0.09 | 30 |
| G15_C3/$V_\kappa3$ | 2 | 3.20E+05 | 1.25E−04 | 0.39 | 0.06 | — |
| G47_B10/$V_\kappa3$ | 3 | 3.74E+05 | 9.12E−04 | 0.24 | 0.1 | — |
| G50_C10/$V_\kappa3$ | 4 | 2.83E+05 | 1.54E−05 | 0.054 | 0.12 | — |

In a further study, surface plasmon resonance (SPR) was conducted using a Biacore 3000 instrument (GE Healthcare) with CM5 sensor chips coupled with mAbs (~500-700 resonance units) using amine-coupling chemistry as described by the manufacturer. The coupling was performed by injecting 2 µg/ml of each protein into 10 mM sodium acetate, pH 4.5 (GE Healthcare), using the amine coupling kit (GE Healthcare). HBS-P buffer pH 7.4 (0.01 M HEPES, 0.15 M NaCl, 0.005% surfactant P20) or phosphate buffer pH 6.0 (67 mM phosphate buffer, 0.15 M NaCl, 0.005% Tween 20) were used as running buffer and dilution buffer. Binding kinetics were determined by injecting titrated amounts of monomeric His-tagged hFcRn (400.0-12.5 nM) over immobilized Abs at pH 7.4 or pH 6.0. All SPR experiments were conducted at 25° C. with a flow rate of 40 µl/min Binding data were zero-adjusted, and the reference cell value subtracted. The Langmuir 1:1 ligand binding model provided by the BIAevaluation software (version 4.1) was used to determine the binding kinetics. The closeness of the fit is described by the statistical value $\chi^2$.

FIG. 7 shows plots of binding association and dissociation for (A) SYNT002h (humanized parent $V_H1/V\kappa1$), (B) SYNT002-3 (G15_C3/$V_\kappa3$), (C) SYNT002-8 (G47_B10/V$\kappa$3), (D) SYNT002-16 (G50_C10/$V_\kappa3$), (E) SYNT002-17 (G54_D11/$V_\kappa3$), and (F) SYNT002-21 (G49_H9.3/$V_\kappa3$), determined by surface plasmon resonance. Kinetic rate constants are provide in Table 6, below. The kinetic rate constants were obtained using a simple first-order (1:1) Langmuir bimolecular interaction model. The kinetic values represent the average of duplicates. The $\chi^2$ (chi-square) values represent the fit to the binding model used.

TABLE 6

Binding kinetics of anti-human FcRn mAbs

| mAbs | $K_a$ (1/Ms) | $K_d$ (1/s) | $K_D$ (nM) | $\chi^2$ |
|---|---|---|---|---|
| pH 7.4 | | | | |
| $V_H1/V\kappa1$ | 1.7 ± 0.1E+05 | 5.1 ± 0.1E-03 | 30.0 | 5.0 |
| G15_C3/$V_\kappa$3 | 0.9 ± 0.2E+05 | 0.7 ± 0.0E-03 | 7.8 | 4.0 |
| G47_B10/$V_\kappa$3 | 1.5 ± 0.1E+05 | 0.6 ± 0.0E-03 | 4.0 | 0.9 |
| G50_C10/$V_\kappa$3 | 1.2 ± 0.1E+05 | 0.00008 ± 0.0E-03 | 0.00066 | 0.6 |
| G54_D11/$V_\kappa$3 | 2.2 ± 0.1E+05 | 7.5 ± 0.0E-03 | 34.0 | 5.0 |
| G49_H9.3/$V_\kappa$3 | 1.8 ± 0.1E+05 | 1.8 ± 0.1E-03 | 10.0 | 3.9 |
| pH 6.0 | | | | |
| $V_H1/V\kappa1$ | 4.5 ± 0.5E+05 | 1.3 ± 0.1E-03 | 2.8 | 11.7 |
| G15_C3/$V_\kappa$3 | 2.7 ± 0.1E+05 | 0.2 ± 0.0E-03 | 0.7 | 27.0 |
| G47_B10/$V_\kappa$3 | 3.5 ± 0.2E+05 | 0.2 ± 0.1E-03 | 0.6 | 5.5 |
| G50_C10/$V_\kappa$3 | 1.1 ± 1.0E+05 | 0.047 ± 0.2E-03 | 0.4 | 2.1 |
| G54_D11/$V_\kappa$3 | 5.9 ± 0.3E+05 | 0.8 ± 0.1E-03 | 1.6 | 36.0 |
| G49_H9.3/$V_\kappa$3 | 5.3 ± 0.3E+05 | 0.9 ± 0.0E-03 | 1.7 | 20.0 |

The results show that all of the antibodies bind human FcRn with distinct kinetics at both pH conditions. The affinity matured variants bound human FcRn with improved affinity at both pH conditions compared to the humanized parent, except for G54_D11/$V_\kappa$3, which was only improved at pH 6.0.

Example 7

Albumin Clearance Study

An in vivo study using transgeneic mice was conducted to examine the effects of anti-FcRn antibodies on albumin clearance. On Day 0, all mice were preloaded by IV injection with 500 mg/kg human albumin Each group of mice (n=6) was dosed with PBS or either G47_B10/$V_\kappa$3 (SYNT002-8) or G50_C10/$V_\kappa$3 (SYNT002-16) at 20 mg/kg on Day 1. Blood samples were collected from each mouse at 24, 32, 48, 56, 72, 96, 120, and 144 hours post IV injection and processed to plasma. Plasma concentrations of albumin were quantified by ELISA.

Figure 8A:
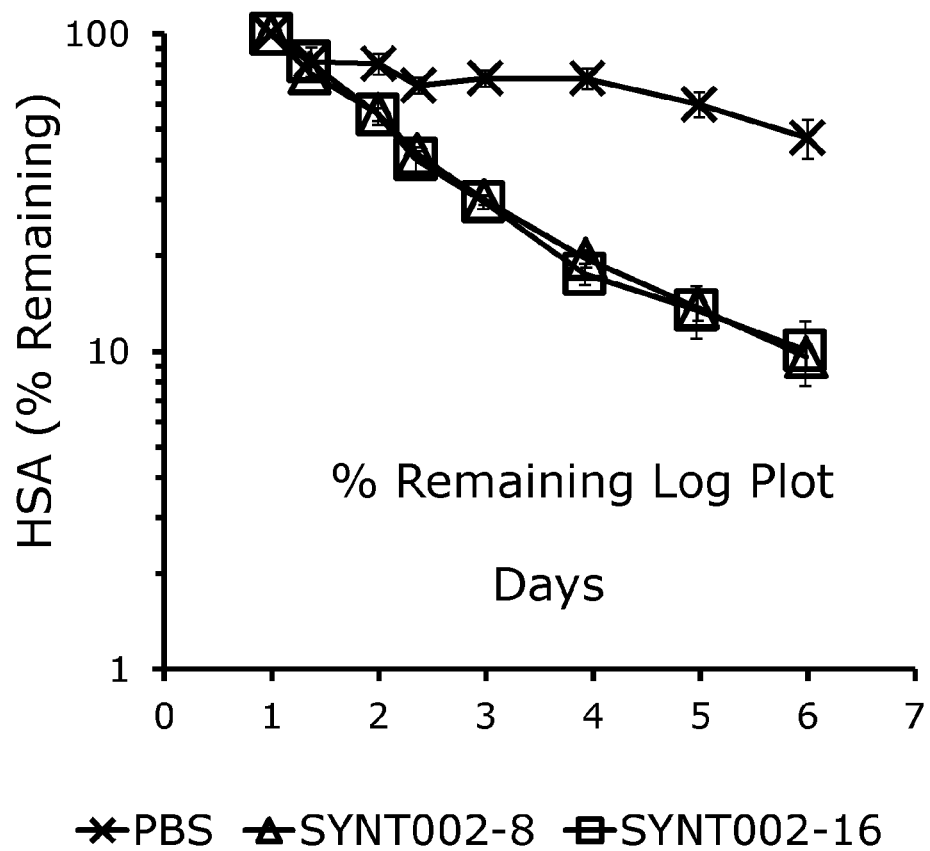
FIG. 8A shows the results of the study of SYNT002-8 (G47_B10/$V_\kappa3$) and SYNT002-16 (G50_C10/$V_\kappa3$) plotted as the mean % albumin remaining based on the 24 hour baselines (±standard error) at the indicated time points.

FIG. 8A shows the results of the study of SYNT002-8 (G47_B10/$V_\kappa$3) and SYNT002-16 (G50_C10/$V_\kappa$3) plotted as the mean % albumin remaining based on the 24 hour baselines (±standard error) at the indicated time points.

Figure 8B:
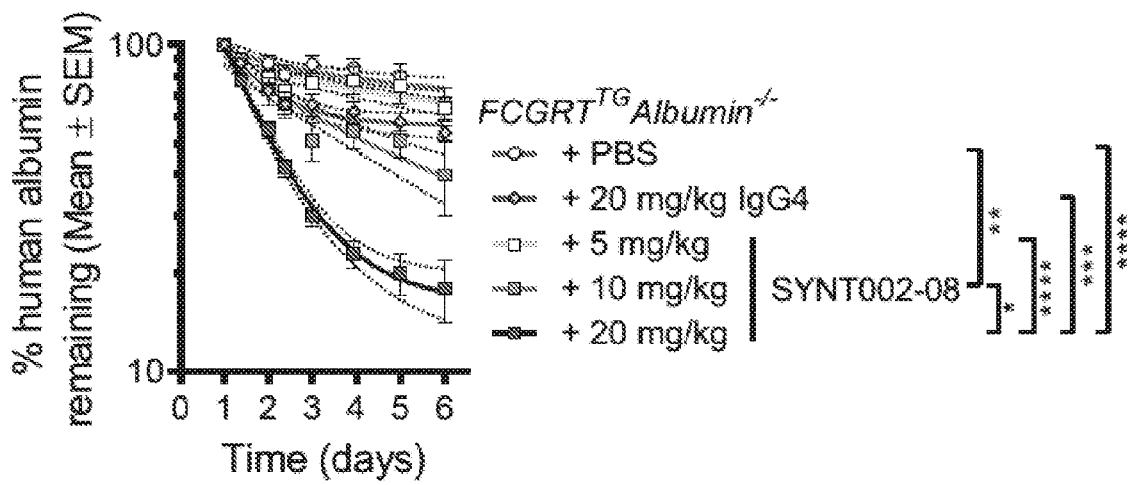
FIG. 8B shows that SYNT002-8 (G47_B10/$V_\kappa3$) effectively increased albumin catabolism in a dose-dependent manner. Results are presented as the $\log_{10}$ of the mean percentage (±SEM) of human albumin remaining at the indicated time points compared with the 24 hour baseline.

FIG. 8B shows the results of a second experiment demonstrating that SYNT002-8 (G47_B10/$V_\kappa$3) effectively increased albumin catabolism in a dose-dependent manner PBS, IgG4 isotype control (20 mg/kg), and three different concentrations of SYNT002-8 (G47_B10/$V_\kappa$3) (5 mg/kg, 10 mg/kg, and 20 mg/kg) were administered, and the results are presented as the login of the mean percentage (±SEM) of human albumin remaining at the indicated time points compared with the 24 hour baseline. Curves represent a nonlinear regression analysis with 90% confidence intervals. The slopes of these curves±SD were analyzed by oneway ANOVA (n=5-11; *P=0.031; P=0.0069; *P=0.0003; ****P<0.0001).

Example 8

Acetaminophen (APAP) Protection Study

An in vivo study using transgeneic mice was conducted to examine the protective effects of anti-FcRn antibodies against acetaminophen (APAP) hepatotoxicity. To do so, a sublethal dose of APAP (400 mg/kg) was administered to Fcgrt$^{TG}$ mice. PBS, the standard clinical antidote N-acetylcystein (NAC) (140 mg/kg), SYNT002-8 (G47_B10/$V_\kappa$3) (10 mg/kg), or IgG4 isotype control (10 mg/kg) was administered two hours after APAP administration. Serum alanine aminotransferase (ALT) levels were measured six and eight hours after APAP administration.

Figure 9:
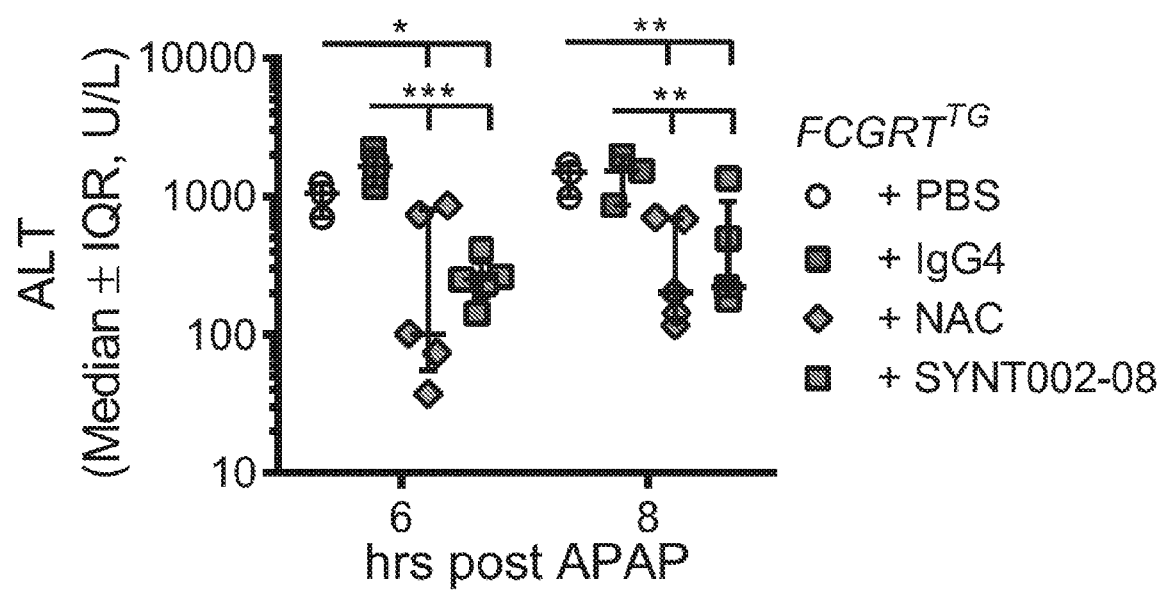
FIG. 9 shows serum ALT levels six and eight hours after sublevel APAP administration in Fcgrt$^{TG}$ mice that received PCS, NAC (140 mg/kg), SYNT002-8 (G47_B10/$V_\kappa3$) (10 mg/kg), or IgG4 isotype control (10 mg/kg) two hours after APAP administration.

FIG. 9 shows that SYNT002-8 (G47_B10/$V_\kappa$3) at a dose of 10 mg/kg provided protection to Fcgrt$^{TG}$ mice equivalent to that provided by NAC administered two hours after sublethal APAP challenge when compared with the control treatment (n=3-5; *P<0.05; P<0.0038; *P<0.001). Accordingly, in a therapeutic setting, SYNT002-8 confers protection from toxic APAP exposure to the same extent as current standard antidote NAC.

We claim:

1. An antibody or antigen-binding fragment thereof which binds to neonatal Fc receptor (FcRn) comprising a heavy chain variable region and a variable chain variable region, the heavy chain variable region comprising a CDR1H, CDR2H, and CDR3H and the light chain variable region comprising a CDR1L, CDR2L, and CDR3L wherein: the sequence of CDR1H comprises SEQ ID NO:2; the sequence of CDR2H comprises SEQ ID NO:4; the sequence of CDR3H comprises SEQ ID NO:27; the sequence of CDR1L comprises SEQ ID NO:6; the sequence of CDR2L comprises SEQ ID NO: 8; and the sequence of CDR3L comprises SEQ ID NO: 10.

2. The antibody or antigen-binding fragment of claim 1, wherein the sequence of the heavy chain variable region comprises SEQ ID NO:28 and the sequence of the light chain variable region comprises SEQ ID NO:22.

3. The antibody or antigen-binding fragment of claim 1, wherein the antibody or antigen-binding fragment is a chimeric antibody or antigen-binding fragment or a humanized antibody or antigen-binding fragment.

4. The antibody of claim 1, which has isotype IgG4.

5. The antibody of claim 4 containing S241P modifications in the heavy chains.

6. The antibody of claim 4 lacking C-terminal lysines in the heavy chains.

7. The antibody or antigen-binding fragment of claim 1, which is an scFv, Fv, Fab', Fab, F(ab')$_2$, or diabody.

8. A composition comprising an FcRn antibody or antigen-binding fragment of claim 1, and a pharmaceutically acceptable carrier.

9. A method of modulating the interaction between FcRn and albumin, the method comprising contacting FcRn with an antibody or antigen-binding fragment of claim 1.

* * * * *

SEQUENCE LISTING

```
<160> NUMBER OF SEQ ID NOS: 48

<210> SEQ ID NO 1
<211> LENGTH: 15
<212> TYPE: DNA
<213> ORGANISM: Mus musculus
<220> FEATURE:
<221> NAME/KEY: CDS
<222> LOCATION: (1)..(15)

<400> SEQUENCE: 1
```

```
gac tat gga atg cac                                              15
Asp Tyr Gly Met His
1               5

<210> SEQ ID NO 2
<211> LENGTH: 5
<212> TYPE: PRT
<213> ORGANISM: Mus musculus

<400> SEQUENCE: 2

Asp Tyr Gly Met His
1               5

<210> SEQ ID NO 3
<211> LENGTH: 51
<212> TYPE: DNA
<213> ORGANISM: Mus musculus
<220> FEATURE:
<221> NAME/KEY: CDS
<222> LOCATION: (1)..(51)

<400> SEQUENCE: 3 tac att agt agt ggc agt agt acc atc tac tat gca gac aca gtg aag    48
Tyr Ile Ser Ser Gly Ser Ser Thr Ile Tyr Tyr Ala Asp Thr Val Lys
1               5                   10                  15 ggc                                                                51
Gly

<210> SEQ ID NO 4
<211> LENGTH: 17
<212> TYPE: PRT
<213> ORGANISM: Mus musculus

<400> SEQUENCE: 4

Tyr Ile Ser Ser Gly Ser Ser Thr Ile Tyr Tyr Ala Asp Thr Val Lys
1               5                   10                  15

Gly

<210> SEQ ID NO 5
<211> LENGTH: 33
<212> TYPE: DNA
<213> ORGANISM: Mus musculus
<220> FEATURE:
<221> NAME/KEY: CDS
<222> LOCATION: (1)..(33)

<400> SEQUENCE: 5 aag gcc agt cag agt gtg agt aat gat gta gct                        33
Lys Ala Ser Gln Ser Val Ser Asn Asp Val Ala
1               5                   10

<210> SEQ ID NO 6
<211> LENGTH: 11
<212> TYPE: PRT
<213> ORGANISM: Mus musculus

<400> SEQUENCE: 6

Lys Ala Ser Gln Ser Val Ser Asn Asp Val Ala
1               5                   10

<210> SEQ ID NO 7
<211> LENGTH: 21
<212> TYPE: DNA
<213> ORGANISM: Mus musculus
<220> FEATURE:
```

```
<221> NAME/KEY: CDS
<222> LOCATION: (1)..(21)

<400> SEQUENCE: 7 tat gca tcc aat cgc tac act                                    21
Tyr Ala Ser Asn Arg Tyr Thr
1               5

<210> SEQ ID NO 8
<211> LENGTH: 7
<212> TYPE: PRT
<213> ORGANISM: Mus musculus

<400> SEQUENCE: 8

Tyr Ala Ser Asn Arg Tyr Thr
1               5

<210> SEQ ID NO 9
<211> LENGTH: 24
<212> TYPE: DNA
<213> ORGANISM: Mus musculus
<220> FEATURE:
<221> NAME/KEY: CDS
<222> LOCATION: (1)..(24)

<400> SEQUENCE: 9 cag cag gat tat agc tct ctc acg                                24
Gln Gln Asp Tyr Ser Ser Leu Thr
1               5

<210> SEQ ID NO 10
<211> LENGTH: 8
<212> TYPE: PRT
<213> ORGANISM: Mus musculus

<400> SEQUENCE: 10

Gln Gln Asp Tyr Ser Ser Leu Thr
1               5

<210> SEQ ID NO 11
<211> LENGTH: 357
<212> TYPE: DNA
<213> ORGANISM: Artificial Sequence
<220> FEATURE:
<223> OTHER INFORMATION: Humanized
<220> FEATURE:
<221> NAME/KEY: CDS
<222> LOCATION: (1)..(357)
<220> FEATURE:
<221> NAME/KEY: misc_feature
<222> LOCATION: (91)..(105)
<223> OTHER INFORMATION: CDR
<220> FEATURE:
<221> NAME/KEY: misc_feature
<222> LOCATION: (148)..(198)
<223> OTHER INFORMATION: CDR
<220> FEATURE:
<221> NAME/KEY: misc_feature
<222> LOCATION: (295)..(324)
<223> OTHER INFORMATION: CDR

<400> SEQUENCE: 11 gag gtg cag ctg gtg gag tct ggg gga ggc tta gtg aag cct gga ggg    48
Glu Val Gln Leu Val Glu Ser Gly Gly Gly Leu Val Lys Pro Gly Gly
1               5                   10                  15 tcc ctg aaa ctc tcc tgt gca gcc tct gga ttc act ttc agt nnn nnn    96
Ser Leu Lys Leu Ser Cys Ala Ala Ser Gly Phe Thr Phe Ser Xaa Xaa
            20                  25                  30
```

```
nnn nnn nnn tgg gtt cgt cag gct cca ggg aag ggg ctg gag tgg gtt        144
Xaa Xaa Xaa Trp Val Arg Gln Ala Pro Gly Lys Gly Leu Glu Trp Val
        35                  40                  45 gca nnn nnn nnn nnn nnn nnn nnn nnn nnn nnn nnn nnn nnn nnn nnn        192
Ala Xaa Xaa Xaa Xaa Xaa Xaa Xaa Xaa Xaa Xaa Xaa Xaa Xaa Xaa Xaa
    50                  55                  60 nnn nnn cga ttc acc atc tcc aga gac aat gcc aag aac acc ctg tat        240
Xaa Xaa Arg Phe Thr Ile Ser Arg Asp Asn Ala Lys Asn Thr Leu Tyr
65                  70                  75                  80 ctg caa atg aac agt ctg agg gcc gag gac acg gcc atg tat tac tgt        288
Leu Gln Met Asn Ser Leu Arg Ala Glu Asp Thr Ala Met Tyr Tyr Cys
                85                  90                  95 gca agg nnn nnn nnn nnn nnn nnn nnn nnn nnn tgg ggt caa gga            336
Ala Arg Xaa Xaa Xaa Xaa Xaa Xaa Xaa Xaa Xaa Trp Gly Gln Gly
            100                 105                 110 acc tca gtc acc gtc tcc tca                                            357
Thr Ser Val Thr Val Ser Ser
        115
```

<210> SEQ ID NO 12
<211> LENGTH: 119
<212> TYPE: PRT
<213> ORGANISM: Artificial Sequence
<220> FEATURE:
<221> NAME/KEY: misc_feature
<222> LOCATION: (31)..(31)
<223> OTHER INFORMATION: The 'Xaa' at location 31 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (32)..(32)
<223> OTHER INFORMATION: The 'Xaa' at location 32 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (33)..(33)
<223> OTHER INFORMATION: The 'Xaa' at location 33 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (34)..(34)
<223> OTHER INFORMATION: The 'Xaa' at location 34 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (35)..(35)
<223> OTHER INFORMATION: The 'Xaa' at location 35 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (50)..(50)
<223> OTHER INFORMATION: The 'Xaa' at location 50 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (51)..(51)
<223> OTHER INFORMATION: The 'Xaa' at location 51 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (52)..(52)
<223> OTHER INFORMATION: The 'Xaa' at location 52 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature

```
<222> LOCATION: (53)..(53)
<223> OTHER INFORMATION: The 'Xaa' at location 53 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (54)..(54)
<223> OTHER INFORMATION: The 'Xaa' at location 54 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (55)..(55)
<223> OTHER INFORMATION: The 'Xaa' at location 55 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (56)..(56)
<223> OTHER INFORMATION: The 'Xaa' at location 56 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (57)..(57)
<223> OTHER INFORMATION: The 'Xaa' at location 57 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (58)..(58)
<223> OTHER INFORMATION: The 'Xaa' at location 58 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (59)..(59)
<223> OTHER INFORMATION: The 'Xaa' at location 59 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (60)..(60)
<223> OTHER INFORMATION: The 'Xaa' at location 60 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (61)..(61)
<223> OTHER INFORMATION: The 'Xaa' at location 61 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (62)..(62)
<223> OTHER INFORMATION: The 'Xaa' at location 62 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (63)..(63)
<223> OTHER INFORMATION: The 'Xaa' at location 63 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (64)..(64)
<223> OTHER INFORMATION: The 'Xaa' at location 64 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (65)..(65)
<223> OTHER INFORMATION: The 'Xaa' at location 65 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (66)..(66)
```

```
<223> OTHER INFORMATION: The 'Xaa' at location 66 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (99)..(99)
<223> OTHER INFORMATION: The 'Xaa' at location 99 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (100)..(100)
<223> OTHER INFORMATION: The 'Xaa' at location 100 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (101)..(101)
<223> OTHER INFORMATION: The 'Xaa' at location 101 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (102)..(102)
<223> OTHER INFORMATION: The 'Xaa' at location 102 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (103)..(103)
<223> OTHER INFORMATION: The 'Xaa' at location 103 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (104)..(104)
<223> OTHER INFORMATION: The 'Xaa' at location 104 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (105)..(105)
<223> OTHER INFORMATION: The 'Xaa' at location 105 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (106)..(106)
<223> OTHER INFORMATION: The 'Xaa' at location 106 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (107)..(107)
<223> OTHER INFORMATION: The 'Xaa' at location 107 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (108)..(108)
<223> OTHER INFORMATION: The 'Xaa' at location 108 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<223> OTHER INFORMATION: Synthetic Construct

<400> SEQUENCE: 12

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Xaa Xaa
            20                  25                  30

Xaa Xaa Xaa Trp Val Arg Gln Ala Pro Gly Lys Gly Leu Glu Trp Val
        35                  40                  45

Ala Xaa Xaa Xaa Xaa Xaa Xaa Xaa Xaa Xaa Xaa Xaa Xaa Xaa Xaa Xaa
    50                  55                  60
```

```
Xaa Xaa Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Met Tyr Tyr Cys
                 85                  90                  95

Ala Arg Xaa Xaa Xaa Xaa Xaa Xaa Xaa Xaa Xaa Trp Gly Gln Gly
            100                 105                 110

Thr Ser Val Thr Val Ser Ser
        115

<210> SEQ ID NO 13
<211> LENGTH: 357
<212> TYPE: DNA
<213> ORGANISM: Artificial Sequence
<220> FEATURE:
<223> OTHER INFORMATION: Humanized
<220> FEATURE:
<221> NAME/KEY: CDS
<222> LOCATION: (1)..(357)
<220> FEATURE:
<221> NAME/KEY: misc_feature
<222> LOCATION: (91)..(105)
<223> OTHER INFORMATION: CDR
<220> FEATURE:
<221> NAME/KEY: misc_feature
<222> LOCATION: (148)..(198)
<223> OTHER INFORMATION: CDR
<220> FEATURE:
<221> NAME/KEY: misc_feature
<222> LOCATION: (295)..(324)
<223> OTHER INFORMATION: CDR

<400> SEQUENCE: 13 gag gtg cag ctg gtg gag tct ggg gga ggc tta gtg aag cct gga ggg    48
Glu Val Gln Leu Val Glu Ser Gly Gly Gly Leu Val Lys Pro Gly Gly
 1               5                  10                  15 tcc ctg aaa ctc tcc tgt gca gcc tct gga ttc act ttc agt nnn nnn    96
Ser Leu Lys Leu Ser Cys Ala Ala Ser Gly Phe Thr Phe Ser Xaa Xaa
                20                  25                  30 nnn nnn nnn tgg gtt cgt cag gct cca ggg aag ggg ctg gag tgg gtt   144
Xaa Xaa Xaa Trp Val Arg Gln Ala Pro Gly Lys Gly Leu Glu Trp Val
            35                  40                  45 gca nnn nnn nnn nnn nnn nnn nnn nnn nnn nnn nnn nnn nnn nnn nnn   192
Ala Xaa Xaa Xaa Xaa Xaa Xaa Xaa Xaa Xaa Xaa Xaa Xaa Xaa Xaa Xaa
    50                  55                  60 nnn nnn cga ttc acc atc tcc aga gac aat gcc aag aac acc ctg tat   240
Xaa Xaa Arg Phe Thr Ile Ser Arg Asp Asn Ala Lys Asn Thr Leu Tyr
 65                  70                  75                  80 ctg caa atg aac agt ctg agg gcc gag gac acg gcc gtg tat tac tgt   288
Leu Gln Met Asn Ser Leu Arg Ala Glu Asp Thr Ala Val Tyr Tyr Cys
                 85                  90                  95 gca agg nnn nnn nnn nnn nnn nnn nnn nnn nnn tgg ggt caa gga        336
Ala Arg Xaa Xaa Xaa Xaa Xaa Xaa Xaa Xaa Xaa Trp Gly Gln Gly
            100                 105                 110 acc acg gtc acc gtc tcc tca                                        357
Thr Thr Val Thr Val Ser Ser
        115

<210> SEQ ID NO 14
<211> LENGTH: 119
<212> TYPE: PRT
<213> ORGANISM: Artificial Sequence
<220> FEATURE:
<221> NAME/KEY: misc_feature
<222> LOCATION: (31)..(31)
<223> OTHER INFORMATION: The 'Xaa' at location 31 stands for Lys, Asn,
```

```
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (32)..(32)
<223> OTHER INFORMATION: The 'Xaa' at location 32 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (33)..(33)
<223> OTHER INFORMATION: The 'Xaa' at location 33 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (34)..(34)
<223> OTHER INFORMATION: The 'Xaa' at location 34 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (35)..(35)
<223> OTHER INFORMATION: The 'Xaa' at location 35 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (50)..(50)
<223> OTHER INFORMATION: The 'Xaa' at location 50 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (51)..(51)
<223> OTHER INFORMATION: The 'Xaa' at location 51 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (52)..(52)
<223> OTHER INFORMATION: The 'Xaa' at location 52 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (53)..(53)
<223> OTHER INFORMATION: The 'Xaa' at location 53 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (54)..(54)
<223> OTHER INFORMATION: The 'Xaa' at location 54 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (55)..(55)
<223> OTHER INFORMATION: The 'Xaa' at location 55 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (56)..(56)
<223> OTHER INFORMATION: The 'Xaa' at location 56 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (57)..(57)
<223> OTHER INFORMATION: The 'Xaa' at location 57 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (58)..(58)
<223> OTHER INFORMATION: The 'Xaa' at location 58 stands for Lys, Asn,
      Arg, Ser, Thr, Ile, Met, Glu, Asp, Gly, Ala, Val, Gln, His, Pro,
```

```
      Leu, Tyr, Trp, Cys, or Phe.
<220> FEATURE:
<221> NAME/KEY: misc_feature
<222> LOCATION: (59)..(59)
<223> OTHER INFORMATION: The 'Xaa' at location 59 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (60)..(60)
<223> OTHER INFORMATION: The 'Xaa' at location 60 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (61)..(61)
<223> OTHER INFORMATION: The 'Xaa' at location 61 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (62)..(62)
<223> OTHER INFORMATION: The 'Xaa' at location 62 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (63)..(63)
<223> OTHER INFORMATION: The 'Xaa' at location 63 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (64)..(64)
<223> OTHER INFORMATION: The 'Xaa' at location 64 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (65)..(65)
<223> OTHER INFORMATION: The 'Xaa' at location 65 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (66)..(66)
<223> OTHER INFORMATION: The 'Xaa' at location 66 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (99)..(99)
<223> OTHER INFORMATION: The 'Xaa' at location 99 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (100)..(100)
<223> OTHER INFORMATION: The 'Xaa' at location 100 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (101)..(101)
<223> OTHER INFORMATION: The 'Xaa' at location 101 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (102)..(102)
<223> OTHER INFORMATION: The 'Xaa' at location 102 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (103)..(103)
<223> OTHER INFORMATION: The 'Xaa' at location 103 stands for Lys, Asn,
      Arg, Ser, Thr, Ile, Met, Glu, Asp, Gly, Ala, Val, Gln, His, Pro,
      Leu, Tyr, Trp, Cys, or Phe.
```

```
<220> FEATURE:
<221> NAME/KEY: misc_feature
<222> LOCATION: (104)..(104)
<223> OTHER INFORMATION: The 'Xaa' at location 104 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (105)..(105)
<223> OTHER INFORMATION: The 'Xaa' at location 105 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (106)..(106)
<223> OTHER INFORMATION: The 'Xaa' at location 106 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (107)..(107)
<223> OTHER INFORMATION: The 'Xaa' at location 107 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (108)..(108)
<223> OTHER INFORMATION: The 'Xaa' at location 108 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<223> OTHER INFORMATION: Synthetic Construct

<400> SEQUENCE: 14

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Xaa Xaa
            20                  25                  30

Xaa Xaa Xaa Trp Val Arg Gln Ala Pro Gly Lys Gly Leu Glu Trp Val
        35                  40                  45

Ala Xaa Xaa Xaa Xaa Xaa Xaa Xaa Xaa Xaa Xaa Xaa Xaa Xaa Xaa Xaa
    50                  55                  60

Xaa Xaa Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Xaa Xaa Xaa Xaa Xaa Xaa Xaa Xaa Xaa Trp Gly Gln Gly
            100                 105                 110

Thr Thr Val Thr Val Ser Ser
        115

<210> SEQ ID NO 15
<211> LENGTH: 357
<212> TYPE: DNA
<213> ORGANISM: Artificial Sequence
<220> FEATURE:
<223> OTHER INFORMATION: Humanized
<220> FEATURE:
<221> NAME/KEY: CDS
<222> LOCATION: (1)..(357)
<220> FEATURE:
<221> NAME/KEY: misc_feature
<222> LOCATION: (91)..(105)
<223> OTHER INFORMATION: CDR
<220> FEATURE:
<221> NAME/KEY: misc_feature
<222> LOCATION: (148)..(198)
<223> OTHER INFORMATION: CDR
<220> FEATURE:
<221> NAME/KEY: misc_feature
```

<222> LOCATION: (295)..(324)
<223> OTHER INFORMATION: CDR

<400> SEQUENCE: 15

```
gag gtg cag ctg gtg gag tct ggg gga ggc tta gtg aag cct gga ggg      48
Glu Val Gln Leu Val Glu Ser Gly Gly Gly Leu Val Lys Pro Gly Gly
1               5                   10                  15 tcc ctg aaa ctc tcc tgt gca gcc tct gga ttc act ttc agt nnn nnn      96
Ser Leu Lys Leu Ser Cys Ala Ala Ser Gly Phe Thr Phe Ser Xaa Xaa
            20                  25                  30 nnn nnn nnn tgg gtt cgt cag gct cca ggg aag ggg ctg gag tgg gtt     144
Xaa Xaa Xaa Trp Val Arg Gln Ala Pro Gly Lys Gly Leu Glu Trp Val
        35                  40                  45 gca nnn nnn nnn nnn nnn nnn nnn nnn nnn nnn nnn nnn nnn nnn         192
Ala Xaa Xaa Xaa Xaa Xaa Xaa Xaa Xaa Xaa Xaa Xaa Xaa Xaa Xaa
    50                  55                  60 nnn nnn cga ttc acc atc tcc aga gac aat gcc aag aac acc ctg tat     240
Xaa Xaa Arg Phe Thr Ile Ser Arg Asp Asn Ala Lys Asn Thr Leu Tyr
65                  70                  75                  80 ctg caa atg aac agt ctg agg tct gag gac acg gcc atg tat tac tgt     288
Leu Gln Met Asn Ser Leu Arg Ser Glu Asp Thr Ala Met Tyr Tyr Cys
                85                  90                  95 gca agg nnn nnn nnn nnn nnn nnn nnn nnn nnn nnn tgg ggt caa gga     336
Ala Arg Xaa Xaa Xaa Xaa Xaa Xaa Xaa Xaa Xaa Xaa Trp Gly Gln Gly
            100                 105                 110 acc acg gtc acc gtc tcc tca                                         357
Thr Thr Val Thr Val Ser Ser
            115
```

<210> SEQ ID NO 16
<211> LENGTH: 119
<212> TYPE: PRT
<213> ORGANISM: Artificial Sequence
<220> FEATURE:
<221> NAME/KEY: misc_feature
<222> LOCATION: (31)..(31)
<223> OTHER INFORMATION: The 'Xaa' at location 31 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (32)..(32)
<223> OTHER INFORMATION: The 'Xaa' at location 32 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (33)..(33)
<223> OTHER INFORMATION: The 'Xaa' at location 33 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (34)..(34)
<223> OTHER INFORMATION: The 'Xaa' at location 34 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (35)..(35)
<223> OTHER INFORMATION: The 'Xaa' at location 35 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (50)..(50)
<223> OTHER INFORMATION: The 'Xaa' at location 50 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:

-continued

```
<221> NAME/KEY: misc_feature
<222> LOCATION: (51)..(51)
<223> OTHER INFORMATION: The 'Xaa' at location 51 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (52)..(52)
<223> OTHER INFORMATION: The 'Xaa' at location 52 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (53)..(53)
<223> OTHER INFORMATION: The 'Xaa' at location 53 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (54)..(54)
<223> OTHER INFORMATION: The 'Xaa' at location 54 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (55)..(55)
<223> OTHER INFORMATION: The 'Xaa' at location 55 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (56)..(56)
<223> OTHER INFORMATION: The 'Xaa' at location 56 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (57)..(57)
<223> OTHER INFORMATION: The 'Xaa' at location 57 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (58)..(58)
<223> OTHER INFORMATION: The 'Xaa' at location 58 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (59)..(59)
<223> OTHER INFORMATION: The 'Xaa' at location 59 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (60)..(60)
<223> OTHER INFORMATION: The 'Xaa' at location 60 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (61)..(61)
<223> OTHER INFORMATION: The 'Xaa' at location 61 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (62)..(62)
<223> OTHER INFORMATION: The 'Xaa' at location 62 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (63)..(63)
<223> OTHER INFORMATION: The 'Xaa' at location 63 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
```

```
<222> LOCATION: (64)..(64)
<223> OTHER INFORMATION: The 'Xaa' at location 64 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (65)..(65)
<223> OTHER INFORMATION: The 'Xaa' at location 65 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (66)..(66)
<223> OTHER INFORMATION: The 'Xaa' at location 66 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (99)..(99)
<223> OTHER INFORMATION: The 'Xaa' at location 99 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (100)..(100)
<223> OTHER INFORMATION: The 'Xaa' at location 100 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (101)..(101)
<223> OTHER INFORMATION: The 'Xaa' at location 101 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (102)..(102)
<223> OTHER INFORMATION: The 'Xaa' at location 102 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (103)..(103)
<223> OTHER INFORMATION: The 'Xaa' at location 103 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (104)..(104)
<223> OTHER INFORMATION: The 'Xaa' at location 104 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (105)..(105)
<223> OTHER INFORMATION: The 'Xaa' at location 105 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (106)..(106)
<223> OTHER INFORMATION: The 'Xaa' at location 106 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (107)..(107)
<223> OTHER INFORMATION: The 'Xaa' at location 107 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (108)..(108)
<223> OTHER INFORMATION: The 'Xaa' at location 108 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<223> OTHER INFORMATION: Synthetic Construct
```

-continued

<400> SEQUENCE: 16

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Xaa Xaa
            20                  25                  30

Xaa Xaa Xaa Trp Val Arg Gln Ala Pro Gly Lys Gly Leu Glu Trp Val
        35                  40                  45

Ala Xaa Xaa Xaa Xaa Xaa Xaa Xaa Xaa Xaa Xaa Xaa Xaa Xaa Xaa Xaa
    50                  55                  60

Xaa Xaa Arg Phe Thr Ile Ser Arg Asp Asn Ala Lys Asn Thr Leu Tyr
65                  70                  75                  80

Leu Gln Met Asn Ser Leu Arg Ser Glu Asp Thr Ala Met Tyr Tyr Cys
                85                  90                  95

Ala Arg Xaa Xaa Xaa Xaa Xaa Xaa Xaa Xaa Xaa Xaa Trp Gly Gln Gly
            100                 105                 110

Thr Thr Val Thr Val Ser Ser
        115

<210> SEQ ID NO 17
<211> LENGTH: 318
<212> TYPE: DNA
<213> ORGANISM: Artificial Sequence
<220> FEATURE:
<223> OTHER INFORMATION: Humanized
<220> FEATURE:
<221> NAME/KEY: CDS
<222> LOCATION: (1)..(318)

<400> SEQUENCE: 17 agt att gtg atg acc cag tct ccc gac ttc ctg ctt gca tca gtg gga     48
Ser Ile Val Met Thr Gln Ser Pro Asp Phe Leu Leu Ala Ser Val Gly
1               5                   10                  15 gac agg gtt acc ata acc tgc aag gcc agt cag agt gtg agt aat gat     96
Asp Arg Val Thr Ile Thr Cys Lys Ala Ser Gln Ser Val Ser Asn Asp
            20                  25                  30 gta gct tgg tac caa cag aag cca ggg cag cct cct aaa ctg ctg ata    144
Val Ala Trp Tyr Gln Gln Lys Pro Gly Gln Pro Pro Lys Leu Leu Ile
        35                  40                  45 tac tat gca tcc aat cgc tac act gga gtc cct gat cgc ttc act ggc    192
Tyr Tyr Ala Ser Asn Arg Tyr Thr Gly Val Pro Asp Arg Phe Thr Gly
    50                  55                  60 agt gga tat ggg acg gat ttc act ctc acc atc agc agc ctg cag gct    240
Ser Gly Tyr Gly Thr Asp Phe Thr Leu Thr Ile Ser Ser Leu Gln Ala
65                  70                  75                  80 gaa gac gtg gca gtt tat ttc tgt cag cag gat tat agc tct ctc acg    288
Glu Asp Val Ala Val Tyr Phe Cys Gln Gln Asp Tyr Ser Ser Leu Thr
                85                  90                  95 ttc ggt cag ggg acc aag ctg gag atc aaa                            318
Phe Gly Gln Gly Thr Lys Leu Glu Ile Lys
            100                 105

<210> SEQ ID NO 18
<211> LENGTH: 106
<212> TYPE: PRT
<213> ORGANISM: Artificial Sequence
<220> FEATURE:
<223> OTHER INFORMATION: Synthetic Construct

<400> SEQUENCE: 18

Ser Ile Val Met Thr Gln Ser Pro Asp Phe Leu Leu Ala Ser Val Gly
1               5                   10                  15

```
Asp Arg Val Thr Ile Thr Cys Lys Ala Ser Gln Ser Val Ser Asn Asp
            20                  25                  30

Val Ala Trp Tyr Gln Gln Lys Pro Gly Gln Pro Pro Lys Leu Leu Ile
        35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Leu Thr Ile Ser Ser Leu Gln Ala
65                  70                  75                  80

Glu Asp Val Ala Val Tyr Phe Cys Gln Gln Asp Tyr Ser Ser Leu Thr
                85                  90                  95

Phe Gly Gln Gly Thr Lys Leu Glu Ile Lys
            100                 105

<210> SEQ ID NO 19
<211> LENGTH: 318
<212> TYPE: DNA
<213> ORGANISM: Artificial Sequence
<220> FEATURE:
<223> OTHER INFORMATION: Humanized
<220> FEATURE:
<221> NAME/KEY: CDS
<222> LOCATION: (1)..(318)

<400> SEQUENCE: 19 agt att gtg atg acc cag tct ccc gac tcc ctg tct gca tca gtg gga      48
Ser Ile Val Met Thr Gln Ser Pro Asp Ser Leu Ser Ala Ser Val Gly
1               5                   10                  15 gac agg gtt acc ata acc tgc aag gcc agt cag agt gtg agt aat gat      96
Asp Arg Val Thr Ile Thr Cys Lys Ala Ser Gln Ser Val Ser Asn Asp
            20                  25                  30 gta gct tgg tac caa cag aag cca ggg cag cct cct aaa ctg ctg ata     144
Val Ala Trp Tyr Gln Gln Lys Pro Gly Gln Pro Pro Lys Leu Leu Ile
        35                  40                  45 tac tat gca tcc aat cgc tac act gga gtc cct gat cgc ttc act ggc     192
Tyr Tyr Ala Ser Asn Arg Tyr Thr Gly Val Pro Asp Arg Phe Thr Gly
    50                  55                  60 agt gga tat ggg acg gat ttc act ctc acc atc agc agc ctg cag gct     240
Ser Gly Tyr Gly Thr Asp Phe Thr Leu Thr Ile Ser Ser Leu Gln Ala
65                  70                  75                  80 gaa gac gtg gca gtt tat ttc tgt cag cag gat tat agc tct ctc acg     288
Glu Asp Val Ala Val Tyr Phe Cys Gln Gln Asp Tyr Ser Ser Leu Thr
                85                  90                  95 ttc ggt cag ggg acc aag ctg gag atc aaa                             318
Phe Gly Gln Gly Thr Lys Leu Glu Ile Lys
            100                 105

<210> SEQ ID NO 20
<211> LENGTH: 106
<212> TYPE: PRT
<213> ORGANISM: Artificial Sequence
<220> FEATURE:
<223> OTHER INFORMATION: Synthetic Construct

<400> SEQUENCE: 20

Ser Ile Val Met Thr Gln Ser Pro Asp Ser Leu Ser Ala Ser Val Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Pro Pro Lys Leu Leu Ile
        35                  40                  45
```

```
Tyr Tyr Ala Ser Asn Arg Tyr Thr Gly Val Pro Asp Arg Phe Thr Gly
    50                  55                  60

Ser Gly Tyr Gly Thr Asp Phe Thr Leu Thr Ile Ser Ser Leu Gln Ala
 65                 70                  75                  80

Glu Asp Val Ala Val Tyr Phe Cys Gln Gln Asp Tyr Ser Ser Leu Thr
                85                  90                  95

Phe Gly Gln Gly Thr Lys Leu Glu Ile Lys
            100                 105

<210> SEQ ID NO 21
<211> LENGTH: 318
<212> TYPE: DNA
<213> ORGANISM: Artificial Sequence
<220> FEATURE:
<223> OTHER INFORMATION: Humanized
<220> FEATURE:
<221> NAME/KEY: CDS
<222> LOCATION: (1)..(318)

<400> SEQUENCE: 21 gac att gtg atg acc cag tct ccc gac tcc ctg tct gca tca gtg gga    48
Asp Ile Val Met Thr Gln Ser Pro Asp Ser Leu Ser Ala Ser Val Gly
  1               5                  10                  15 gac agg gtt acc ata acc tgc aag gcc agt cag agt gtg agt aat gat    96
Asp Arg Val Thr Ile Thr Cys Lys Ala Ser Gln Ser Val Ser Asn Asp
                 20                  25                  30 gta gct tgg tac caa cag aag cca ggg cag cct cct aaa ctg ctg ata   144
Val Ala Trp Tyr Gln Gln Lys Pro Gly Gln Pro Pro Lys Leu Leu Ile
             35                  40                  45 tac tat gca tcc aat cgc tac act gga gtc cct gat cgc ttc agt ggc   192
Tyr Tyr Ala Ser Asn Arg Tyr Thr Gly Val Pro Asp Arg Phe Ser Gly
         50                  55                  60 agt gga tat ggg acg gat ttc act ctc acc atc agc agc ctg cag gct   240
Ser Gly Tyr Gly Thr Asp Phe Thr Leu Thr Ile Ser Ser Leu Gln Ala
 65                 70                  75                  80 gaa gac gtg gca gtt tat ttc tgt cag cag gat tat agc tct ctc acg   288
Glu Asp Val Ala Val Tyr Phe Cys Gln Gln Asp Tyr Ser Ser Leu Thr
                85                  90                  95 ttc ggt cag ggg acc aag ctg gag atc aaa                            318
Phe Gly Gln Gly Thr Lys Leu Glu Ile Lys
            100                 105

<210> SEQ ID NO 22
<211> LENGTH: 106
<212> TYPE: PRT
<213> ORGANISM: Artificial Sequence
<220> FEATURE:
<223> OTHER INFORMATION: Synthetic Construct

<400> SEQUENCE: 22

Asp Ile Val Met Thr Gln Ser Pro Asp Ser Leu Ser Ala Ser Val Gly
  1               5                  10                  15

Asp Arg Val Thr Ile Thr Cys Lys Ala Ser Gln Ser Val Ser Asn Asp
                 20                  25                  30

Val Ala Trp Tyr Gln Gln Lys Pro Gly Gln Pro Pro Lys Leu Leu Ile
             35                  40                  45

Tyr Tyr Ala Ser Asn Arg Tyr Thr Gly Val Pro Asp Arg Phe Ser Gly
         50                  55                  60

Ser Gly Tyr Gly Thr Asp Phe Thr Leu Thr Ile Ser Ser Leu Gln Ala
 65                 70                  75                  80

Glu Asp Val Ala Val Tyr Phe Cys Gln Gln Asp Tyr Ser Ser Leu Thr
```

```
                          85                  90                  95
Phe Gly Gln Gly Thr Lys Leu Glu Ile Lys
            100                 105

<210> SEQ ID NO 23
<211> LENGTH: 318
<212> TYPE: DNA
<213> ORGANISM: Artificial Sequence
<220> FEATURE:
<223> OTHER INFORMATION: Humanized
<220> FEATURE:
<221> NAME/KEY: CDS
<222> LOCATION: (1)..(318)

<400> SEQUENCE: 23 gac att gtg atg acc cag tct ccc gac tcc ctg tct gca tca gtg gga      48
Asp Ile Val Met Thr Gln Ser Pro Asp Ser Leu Ser Ala Ser Val Gly
1               5                   10                  15 gac agg gtt acc ata acc tgc aag gcc agt cag agt gtg agt aat gat      96
Asp Arg Val Thr Ile Thr Cys Lys Ala Ser Gln Ser Val Ser Asn Asp
                20                  25                  30 gta gct tgg tac caa cag aag cca ggg cag cct cct aaa ctg ctg ata     144
Val Ala Trp Tyr Gln Gln Lys Pro Gly Gln Pro Pro Lys Leu Leu Ile
            35                  40                  45 tac tat gca tcc aat cgc tac act gga gtc cct gat cgc ttc agt ggc     192
Tyr Tyr Ala Ser Asn Arg Tyr Thr Gly Val Pro Asp Arg Phe Ser Gly
    50                  55                  60 agt gga tat ggg acg gat ttc act ctc acc atc agc agc ctg cag gct     240
Ser Gly Tyr Gly Thr Asp Phe Thr Leu Thr Ile Ser Ser Leu Gln Ala
65                  70                  75                  80 gaa gac gtg gca gtt tat tac tgt cag cag gat tat agc tct ctc acg     288
Glu Asp Val Ala Val Tyr Tyr Cys Gln Gln Asp Tyr Ser Ser Leu Thr
                85                  90                  95 ttc ggt cag ggg acc aag ctg gag atc aaa                             318
Phe Gly Gln Gly Thr Lys Leu Glu Ile Lys
            100                 105

<210> SEQ ID NO 24
<211> LENGTH: 106
<212> TYPE: PRT
<213> ORGANISM: Artificial Sequence
<220> FEATURE:
<223> OTHER INFORMATION: Synthetic Construct

<400> SEQUENCE: 24

Asp Ile Val Met Thr Gln Ser Pro Asp Ser Leu Ser Ala Ser Val Gly
1               5                   10                  15

Asp Arg Val Thr Ile Thr Cys Lys Ala Ser Gln Ser Val Ser Asn Asp
                20                  25                  30

Val Ala Trp Tyr Gln Gln Lys Pro Gly Gln Pro Pro Lys Leu Leu Ile
            35                  40                  45

Tyr Tyr Ala Ser Asn Arg Tyr Thr Gly Val Pro Asp Arg Phe Ser Gly
    50                  55                  60

Ser Gly Tyr Gly Thr Asp Phe Thr Leu Thr Ile Ser Ser Leu Gln Ala
65                  70                  75                  80

Glu Asp Val Ala Val Tyr Tyr Cys Gln Gln Asp Tyr Ser Ser Leu Thr
                85                  90                  95

Phe Gly Gln Gly Thr Lys Leu Glu Ile Lys
            100                 105

<210> SEQ ID NO 25
```

```
<211> LENGTH: 10
<212> TYPE: PRT
<213> ORGANISM: Artificial Sequence
<220> FEATURE:
<223> OTHER INFORMATION: Affinity Matured

<400> SEQUENCE: 25

Gly Glu Ser Thr Thr Thr Val Gly Asp Tyr
1               5                   10

<210> SEQ ID NO 26
<211> LENGTH: 119
<212> TYPE: PRT
<213> ORGANISM: Artificial Sequence
<220> FEATURE:
<223> OTHER INFORMATION: Affinity Matured

<400> SEQUENCE: 26

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Tyr Ile Ser Ser Gly Ser Ser Thr Ile Tyr Tyr Ala Asp Thr Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg Gly Glu Ser Thr Thr Thr Val Gly Asp Tyr Trp Gly Gln Gly
            100                 105                 110

Thr Ser Val Thr Val Ser Ser
        115

<210> SEQ ID NO 27
<211> LENGTH: 10
<212> TYPE: PRT
<213> ORGANISM: Artificial Sequence
<220> FEATURE:
<223> OTHER INFORMATION: Affinity Matured

<400> SEQUENCE: 27

Ala Glu Ser Thr Thr Thr Val Gly Asp Tyr
1               5                   10

<210> SEQ ID NO 28
<211> LENGTH: 119
<212> TYPE: PRT
<213> ORGANISM: Artificial Sequence
<220> FEATURE:
<223> OTHER INFORMATION: Affinity Matured

<400> SEQUENCE: 28

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Tyr Ile Ser Ser Gly Ser Ser Thr Ile Tyr Tyr Ala Asp Thr Val
    50                  55                  60
```

-continued

Lys Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Met Tyr Tyr Cys
             85                  90                  95

Ala Arg Ala Glu Ser Thr Thr Val Gly Asp Tyr Trp Gly Gln Gly
        100                 105                 110

Thr Ser Val Thr Val Ser Ser
        115

<210> SEQ ID NO 29
<211> LENGTH: 10
<212> TYPE: PRT
<213> ORGANISM: Artificial Sequence
<220> FEATURE:
<223> OTHER INFORMATION: Affinity Matured

<400> SEQUENCE: 29

Phe Ser Ser Leu Ser Thr Val Gly Asp Tyr
1               5                   10

<210> SEQ ID NO 30
<211> LENGTH: 119
<212> TYPE: PRT
<213> ORGANISM: Artificial Sequence
<220> FEATURE:
<223> OTHER INFORMATION: Affinity Matured

<400> SEQUENCE: 30

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Tyr Ile Ser Ser Gly Ser Ser Thr Ile Tyr Tyr Ala Asp Thr Val
    50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Met Tyr Tyr Cys
             85                  90                  95

Ala Arg Phe Ser Ser Leu Ser Thr Val Gly Asp Tyr Trp Gly Gln Gly
        100                 105                 110

Thr Ser Val Thr Val Ser Ser
        115

<210> SEQ ID NO 31
<211> LENGTH: 10
<212> TYPE: PRT
<213> ORGANISM: Artificial Sequence
<220> FEATURE:
<223> OTHER INFORMATION: Affinity Matured

<400> SEQUENCE: 31

Leu Glu Ser Thr Thr Ala Val Gly Asp Tyr
1               5                   10

<210> SEQ ID NO 32
<211> LENGTH: 119
<212> TYPE: PRT
<213> ORGANISM: Artificial Sequence
<220> FEATURE:

<223> OTHER INFORMATION: Affinity Matured

<400> SEQUENCE: 32

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Tyr Ile Ser Ser Gly Ser Ser Thr Ile Tyr Tyr Ala Asp Thr Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg Leu Glu Ser Thr Thr Ala Val Gly Asp Tyr Trp Gly Gln Gly
            100                 105                 110

Thr Ser Val Thr Val Ser Ser
        115

<210> SEQ ID NO 33
<211> LENGTH: 10
<212> TYPE: PRT
<213> ORGANISM: Artificial Sequence
<220> FEATURE:
<223> OTHER INFORMATION: Affinity Matured

<400> SEQUENCE: 33

Phe Asp Thr Pro Ala Thr Val Gly Asp Tyr
1               5                   10

<210> SEQ ID NO 34
<211> LENGTH: 119
<212> TYPE: PRT
<213> ORGANISM: Artificial Sequence
<220> FEATURE:
<223> OTHER INFORMATION: Affinity Matured

<400> SEQUENCE: 34

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Tyr Ile Ser Ser Gly Ser Ser Thr Ile Tyr Tyr Ala Asp Thr Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg Phe Asp Thr Pro Ala Thr Val Gly Asp Tyr Trp Gly Gln Gly
            100                 105                 110

Thr Ser Val Thr Val Ser Ser
        115

<210> SEQ ID NO 35
<211> LENGTH: 10
<212> TYPE: PRT

```
<213> ORGANISM: Artificial Sequence
<220> FEATURE:
<223> OTHER INFORMATION: Affinity Matured

<400> SEQUENCE: 35

Phe Asp Thr Pro Ser Thr Val Gly Asp Tyr
1               5                   10

<210> SEQ ID NO 36
<211> LENGTH: 119
<212> TYPE: PRT
<213> ORGANISM: Artificial Sequence
<220> FEATURE:
<223> OTHER INFORMATION: Affinity Matured

<400> SEQUENCE: 36

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Tyr Ile Ser Ser Gly Ser Ser Thr Ile Tyr Tyr Ala Asp Thr Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg Phe Asp Thr Pro Ser Thr Val Gly Asp Tyr Trp Gly Gln Gly
            100                 105                 110

Thr Ser Val Thr Val Ser Ser
        115

<210> SEQ ID NO 37
<211> LENGTH: 10
<212> TYPE: PRT
<213> ORGANISM: Artificial Sequence
<220> FEATURE:
<223> OTHER INFORMATION: Affinity Matured

<400> SEQUENCE: 37

Phe Asp Ser Leu Ser Thr Val Gly Asp Tyr
1               5                   10

<210> SEQ ID NO 38
<211> LENGTH: 119
<212> TYPE: PRT
<213> ORGANISM: Artificial Sequence
<220> FEATURE:
<223> OTHER INFORMATION: Affinity Matured

<400> SEQUENCE: 38

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Tyr Ile Ser Ser Gly Ser Ser Thr Ile Tyr Tyr Ala Asp Thr Val
    50                  55                  60

Lys Gly Arg Phe Thr Ile Ser Arg Asp Asn Ala Lys Asn Thr Leu Tyr
```

```
                65                  70                  75                  80
Leu Gln Met Asn Ser Leu Arg Ala Glu Asp Thr Ala Met Tyr Tyr Cys
                    85                  90                  95

Ala Arg Phe Asp Ser Leu Ser Thr Val Gly Asp Tyr Trp Gly Gln Gly
                100                 105                 110

Thr Ser Val Thr Val Ser Ser
        115

<210> SEQ ID NO 39
<211> LENGTH: 10
<212> TYPE: PRT
<213> ORGANISM: Artificial Sequence
<220> FEATURE:
<223> OTHER INFORMATION: Affinity Matured

<400> SEQUENCE: 39

Leu Glu Ala Val Ser Ala Val Gly Asp Tyr
1               5                  10

<210> SEQ ID NO 40
<211> LENGTH: 119
<212> TYPE: PRT
<213> ORGANISM: Artificial Sequence
<220> FEATURE:
<223> OTHER INFORMATION: Affinity Matured

<400> SEQUENCE: 40

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
                20                  25                  30

Gly Met His Trp Val Arg Gln Ala Pro Gly Lys Gly Leu Glu Trp Val
            35                  40                  45

Ala Tyr Ile Ser Ser Gly Ser Ser Thr Ile Tyr Tyr Ala Asp Thr Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Met Tyr Tyr Cys
                    85                  90                  95

Ala Arg Leu Glu Ala Val Ser Ala Val Gly Asp Tyr Trp Gly Gln Gly
                100                 105                 110

Thr Ser Val Thr Val Ser Ser
        115

<210> SEQ ID NO 41
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
```

```
<222> LOCATION: (16)..(16)
<223> OTHER INFORMATION: n is a, c, g, or t

<400> SEQUENCE: 41
argbnsvvsb ncvncnvcrs c                                              21

<210> SEQ ID NO 42
<211> LENGTH: 18
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t

<400> SEQUENCE: 42
aggnnsnnsn nsnnsrsc                                                  18

<210> SEQ ID NO 43
<211> LENGTH: 6
<212> TYPE: PRT
<213> ORGANISM: Artificial Sequence
<220> FEATURE:
<223> OTHER INFORMATION: Consensus
<220> FEATURE:
<221> NAME/KEY: VARIANT
<222> LOCATION: (1)..(1)
<223> OTHER INFORMATION: Residue is A or L
<220> FEATURE:
<221> NAME/KEY: VARIANT
<222> LOCATION: (6)..(6)
<223> OTHER INFORMATION: Residue is T or R

<400> SEQUENCE: 43

Xaa Glu Ser Thr Thr Xaa
1               5

<210> SEQ ID NO 44
<211> LENGTH: 10
<212> TYPE: PRT
<213> ORGANISM: Artificial Sequence
<220> FEATURE:
<223> OTHER INFORMATION: Consensus
<220> FEATURE:
<221> NAME/KEY: VARIANT
<222> LOCATION: (1)..(1)
<223> OTHER INFORMATION: Residue is A or L
<220> FEATURE:
<221> NAME/KEY: VARIANT
<222> LOCATION: (6)..(6)
<223> OTHER INFORMATION: Residue is T or R

<400> SEQUENCE: 44

Xaa Glu Ser Thr Thr Xaa Val Gly Asp Tyr
1               5                   10

<210> SEQ ID NO 45
```

```
<211> LENGTH: 6
<212> TYPE: PRT
<213> ORGANISM: Artificial Sequence
<220> FEATURE:
<223> OTHER INFORMATION: Consensus
<220> FEATURE:
<221> NAME/KEY: VARIANT
<222> LOCATION: (1)..(1)
<223> OTHER INFORMATION: Residue is G, A, or L
<220> FEATURE:
<221> NAME/KEY: VARIANT
<222> LOCATION: (6)..(6)
<223> OTHER INFORMATION: Residue is T or R

<400> SEQUENCE: 45

Xaa Glu Ser Thr Thr Xaa
1               5

<210> SEQ ID NO 46
<211> LENGTH: 10
<212> TYPE: PRT
<213> ORGANISM: Artificial Sequence
<220> FEATURE:
<223> OTHER INFORMATION: Consensus
<220> FEATURE:
<221> NAME/KEY: VARIANT
<222> LOCATION: (1)..(1)
<223> OTHER INFORMATION: Residue is G, A, or L
<220> FEATURE:
<221> NAME/KEY: VARIANT
<222> LOCATION: (6)..(6)
<223> OTHER INFORMATION: Residue is T or R

<400> SEQUENCE: 46

Xaa Glu Ser Thr Thr Xaa Val Gly Asp Tyr
1               5                   10

<210> SEQ ID NO 47
<211> LENGTH: 6
<212> TYPE: PRT
<213> ORGANISM: Artificial Sequence
<220> FEATURE:
<223> OTHER INFORMATION: Consensus
<220> FEATURE:
<221> NAME/KEY: VARIANT
<222> LOCATION: (1)..(1)
<223> OTHER INFORMATION: Residue is G, A, F, or L
<220> FEATURE:
<221> NAME/KEY: VARIANT
<222> LOCATION: (2)..(2)
<223> OTHER INFORMATION: Residue is E, A, or D
<220> FEATURE:
<221> NAME/KEY: VARIANT
<222> LOCATION: (3)..(3)
<223> OTHER INFORMATION: Residue is S, T, or A
<220> FEATURE:
<221> NAME/KEY: VARIANT
<222> LOCATION: (4)..(4)
<223> OTHER INFORMATION: Residue is T, L, P, or V
<220> FEATURE:
<221> NAME/KEY: VARIANT
<222> LOCATION: (5)..(5)
<223> OTHER INFORMATION: Residue is T, S, or A
<220> FEATURE:
<221> NAME/KEY: VARIANT
<222> LOCATION: (6)..(6)
<223> OTHER INFORMATION: Residue is T or A

<400> SEQUENCE: 47

Xaa Xaa Xaa Xaa Xaa Xaa
1               5

<210> SEQ ID NO 48
```

```
<211> LENGTH: 10
<212> TYPE: PRT
<213> ORGANISM: Artificial Sequence
<220> FEATURE:
<223> OTHER INFORMATION: Consensus
<220> FEATURE:
<221> NAME/KEY: VARIANT
<222> LOCATION: (1)..(1)
<223> OTHER INFORMATION: Residue is G, A, F, or L
<220> FEATURE:
<221> NAME/KEY: VARIANT
<222> LOCATION: (2)..(2)
<223> OTHER INFORMATION: Residue is E, A, or D
<220> FEATURE:
<221> NAME/KEY: VARIANT
<222> LOCATION: (3)..(3)
<223> OTHER INFORMATION: Residue is S, T, or A
<220> FEATURE:
<221> NAME/KEY: VARIANT
<222> LOCATION: (4)..(4)
<223> OTHER INFORMATION: Residue is T, L, P, or V
<220> FEATURE:
<221> NAME/KEY: VARIANT
<222> LOCATION: (5)..(5)
<223> OTHER INFORMATION: Residue is T, S, or A
<220> FEATURE:
<221> NAME/KEY: VARIANT
<222> LOCATION: (6)..(6)
<223> OTHER INFORMATION: Residue is T or A

<400> SEQUENCE: 48

Xaa Xaa Xaa Xaa Xaa Xaa Val Gly Asp Tyr
1               5                   10
```